US012599589B2

(12) United States Patent
Okamoto et al.

(10) Patent No.: US 12,599,589 B2
(45) Date of Patent: Apr. 14, 2026

(54) PROPHYLACTIC AND/OR THERAPEUTIC AGENT FOR CHRONIC PROSTATITIS/CHRONIC PELVIC PAIN SYNDROME

(71) Applicant: NIPPON SHINYAKU CO., LTD., Kyoto (JP)

(72) Inventors: Ken Okamoto, Kyoto (JP); Maki Kurita, Kyoto (JP); Hiroshi Yamaguchi, Kyoto (JP)

(73) Assignee: NIPPON SHINYAKU CO., LTD., Kyoto (JP)

( * ) Notice: Subject to any disclaimer, the term of this patent is extended or adjusted under 35 U.S.C. 154(b) by 920 days.

(21) Appl. No.: 17/788,516

(22) PCT Filed: Dec. 24, 2020

(86) PCT No.: PCT/JP2020/048479
§ 371 (c)(1),
(2) Date: Jun. 23, 2022

(87) PCT Pub. No.: WO2021/132472
PCT Pub. Date: Jul. 1, 2021

(65) Prior Publication Data

US 2023/0094705 A1 Mar. 30, 2023

(30) Foreign Application Priority Data

Dec. 25, 2019 (JP) ................................ 2019-233865

(51) Int. Cl.

| | |
|---|---|
| ***A61K 31/4184*** | (2006.01) |
| ***A61K 31/454*** | (2006.01) |
| ***A61K 31/506*** | (2006.01) |
| ***A61P 13/08*** | (2006.01) |
| ***A61P 29/00*** | (2006.01) |

(52) U.S. Cl.
CPC ........ *A61K 31/4184* (2013.01); *A61K 31/454* (2013.01); *A61K 31/506* (2013.01); *A61P 13/08* (2018.01); *A61P 29/00* (2018.01)

(58) Field of Classification Search
CPC ................................................. A61K 31/4184
See application file for complete search history.

(56) References Cited

U.S. PATENT DOCUMENTS

| | | | |
|---|---|---|---|
| 9,216,968 | B2 | 12/2015 | Otsu |
| 2010/0256188 | A1 | 10/2010 | Pfau et al. |
| 2011/0263556 | A1 | 10/2011 | Priepke et al. |
| 2012/0214786 | A1 | 8/2012 | Priepke et al. |
| 2012/0302608 | A1 | 11/2012 | Hughes et al. |
| 2014/0221339 | A1 | 8/2014 | Otsu |
| 2014/0256739 | A1 | 9/2014 | Bassil et al. |
| 2016/0046612 | A1 | 2/2016 | Otsu |
| 2016/0074394 | A1 | 3/2016 | Bassil et al. |
| 2020/0071280 | A1 | 3/2020 | Okada et al. |

FOREIGN PATENT DOCUMENTS

| | | |
|---|---|---|
| EC | 2011-11324 | 9/2011 |
| EC | 2013-12499 | 3/2013 |
| EC | 2013-13047 | 11/2013 |
| EP | 2 746 265 | 6/2014 |
| EP | 3 372 589 | 9/2018 |
| JP | 2013-508325 | 3/2013 |
| JP | 2015-501784 | 1/2015 |
| WO | 2010/100249 | 9/2010 |
| WO | 2011/023812 | 3/2011 |
| WO | 2011/048004 | 4/2011 |
| WO | 2012/022792 | 2/2012 |
| WO | 2012/022793 | 2/2012 |
| WO | 2012/076673 | 6/2012 |
| WO | 2013/024898 | 2/2013 |
| WO | 2013/067296 | 5/2013 |
| WO | 2017/073709 | 5/2017 |

OTHER PUBLICATIONS

International Search Report issued Mar. 2, 2021 in corresponding International (PCT) Application No. PCT/JP2020/048479, with English translation.
Written Opinion issued Mar. 2, 2021 in corresponding International (PCT) Application No. PCT/JP2020/048479, with English translation.
Krieger, J.N. et al., NIH Consensus Definition and Classification of Prostatitis, JAMA, 1999, 281(3), pp. 236-237.
Orhan, I et al., "Seminal plasma cytokine levels in the diagnosis of chronic pelvic pain syndrome", Int. J. Urol., 2001, 8(9), pp. 495-499.
Desireddi, N.V. et al., "Monocyte chemoattractant protein-1α (MCP) and macrophage inflammatory protein-1 a (MIP) as possible biomarkers for the chronic pelvic pain syndrome", J. Urol., 2008, 179(5), 1857-1862.
Jakobsson, P et al., "Identification of human prostaglandin E synthase: A microsomal, glutathione-dependent, inducible enzyme, constituting a potential novel drug target", Proc. Natl. Acad. Sci. USA, 1999, 96, 7220-7225.
Tanikawa, N. et al., "Identification and Characterization of a Novel Type of Membrane-Associated Prostaglandin E Synthase", Biochem. Biophys. Res. Commun, 2002, 291, 884-889.
Tanioka, T. et al., "Molecular Identification of Cytosolic Prostaglandin E2 Synthase That Is Functionally Coupled with Cyclooxygenase-1 in Immediate Prostaglandin $E_2$ Biosynthesis", J. Biol. Chem, 2000, 275(42), 32775-32782.
Kamei, D. et al., "Potential Role of Microsomal Prostaglandin E Synthase-1 in Tumorigenesis", J. Biol. Chem, 2003, 278(21), 19396-19405.
Sasaki, Y. et al., "Microsomal prostaglandin E synthase-1 is involved in multiple steps of colon carcinogenesis", Oncogene, 2012, 31(24), 2943-2952.

(Continued)

*Primary Examiner* — Yong S. Chong
(74) *Attorney, Agent, or Firm* — Wenderoth, Lind & Ponack, L.L.P.

(57) ABSTRACT

The present invention relates to a prophylactic and/or therapeutic agent for chronic prostatitis/chronic pelvic pain syndrome, the agent containing an mPGES-1 inhibitor as an active ingredient.

3 Claims, 1 Drawing Sheet

(56) References Cited

OTHER PUBLICATIONS

Nakanishi, M. et al., "Genetic Deletion of mPGES-1 Suppresses Intestinal Tumorigenesis", Cancer Res., 2008, 68(9), 3251-3259.
Nausch, B. et al., "The standardized herbal combination BNO 2103 contained in Canephron® N alleviates. inflammatory pain in experimental cystitis and prostatitis", Phytomedicine, 2019, 60, 152987, 7 pages.
Nausch, B. et al., "Canephron® N reduces pain in experimental cystitis and prostatitis putatively by inhibition of PGE2 production", European Urology Supplements, 2016, vol. 15, No. 3, p. e262, Abstract No. 262.
Extended European Search Report issued Dec. 7, 2023 in corresponding European Patent Application No. 20905872.6, 8 pages.
Opposition to Ecuadorian patent application 2022-58286 in Proceeding No. SENADI 2022-58286 dated Jan. 24, 2023.
Giron, D., "Thermal analysis and calorimetric methods in the characterisation of polymorphs and solvates", Thermochimica Acta 248, Elsevier Science B.V., 1995, pp. 1-11.
Garrido, J. Forma y estructura de los cristales, (cited work), Chapter V, p. 204-225, with partial English-language translation.
Gama Ciqueira cited by Raúl Moscoso, Propiedad Intelectual e Innovación Tecnológica en el Ecuador, Ed. Abya-Yala. 2000, pp. 37-38, with partial English-language translation.
Remington's Pharmaceutical Sciences. 16th. Mack Pub. Co. Pennsylvania, 1980, pp. 180-181.
Garcia-Pelayo and Gross R., "Larousse Diccionario básico de la lengua española". Ed. Larousse, Buenos Aires Argentina, 1979, p. 250.
Office Action dated Nov. 10, 2025 in corresponding Philippian Patent Application No. 1-2022-551578.

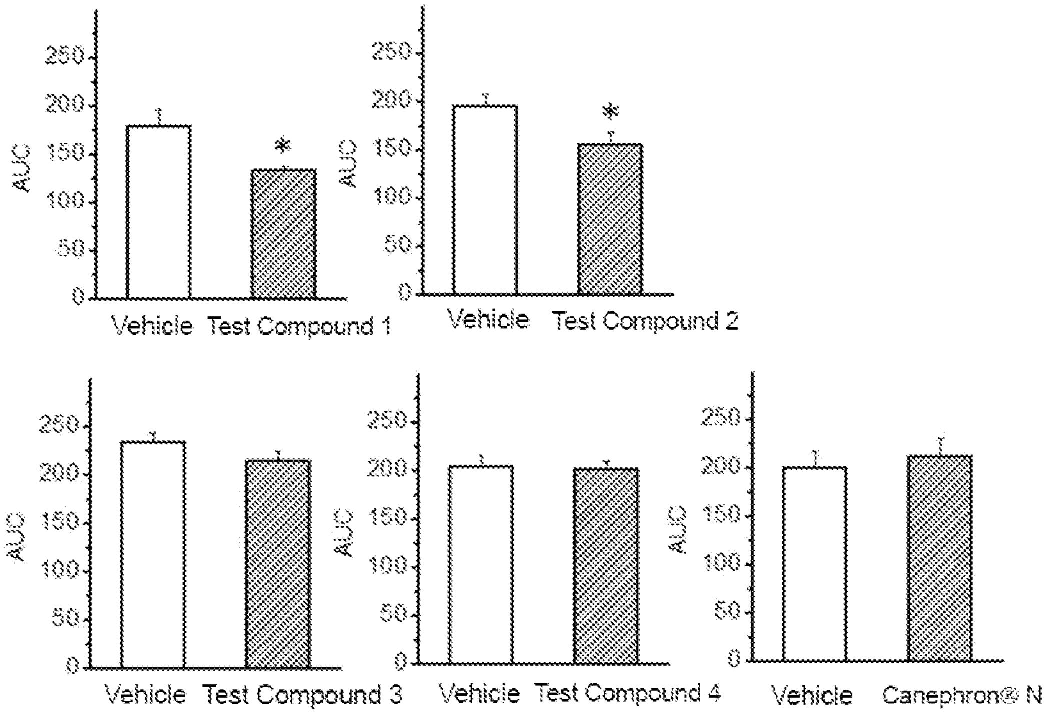
AUC
250
200
150
100
50
0
*
Vehicle
Test Compound 1
Test Compound 2
Test Compound 3
Test Compound 4
Canephron® N

PROPHYLACTIC AND/OR THERAPEUTIC AGENT FOR CHRONIC PROSTATITIS/CHRONIC PELVIC PAIN SYNDROME

TECHNICAL FIELD

The present invention relates to a prophylactic and/or therapeutic agent for chronic prostatitis/chronic pelvic pain syndrome, the agent containing an mPGES-1 inhibitor as an active ingredient.

BACKGROUND ART

Prostatitis is classified into four categories (acute bacterial prostatitis, chronic bacterial prostatitis, chronic prostatitis/chronic pelvic pain syndrome, and asymptomatic inflammatory prostatitis) by the NIH of the United States (Non-Patent Literature 1). Category I is acute bacterial prostatitis associated with systemic symptoms such as urinary symptoms, pain, and fever caused by bacterial infection. Category II is chronic bacterial prostatitis, which is a chronified form of Category I, and symptoms as recurrent bacterial infection are recognized. Category III is chronic prostatitis/chronic pelvic pain syndrome and is classified as diseases having pain and discomfort in the pelvic part such as the perineal part, testicular part, penile part, and lower abdominal part, and voiding symptoms such as a sense of residual urine and pollakiuria, as main symptoms. Additionally, the asymptomatic inflammatory prostatitis of Category IV is a disease without symptoms; however, inflammatory findings are recognized in prostate biopsy tissue specimens or in expressed prostatic secretions and semen. Furthermore, it has been reported that the expression of IL-1β is significantly increased in the seminal plasma of chronic prostatitis patients, and the expression of MIP-la and MCP-1 is significantly increased in the expressed prostatic secretions of chronic prostatitis patients (Non-Patent Literatures 2 and 3).

However, unlike the acute bacterial prostatitis of Category I and the chronic bacterial prostatitis of Category II, the etiology of the chronic prostatitis/chronic pelvic pain syndrome of Category III is not known, and therefore, effective therapeutic methods have not been found.

With regard to PGE2 synthase (PGES), it is known that there are three sub-types such as membrane-bound prostaglandin E synthase-1 (mPGES-1), mPGES-2, and cytoplasmic PGES (cPGES) (Non-Patent Literatures 4 to 6). mPGES-1, in the same manner as COX-2, is primarily induced during inflammation and plays a major part in PGE2 production in inflammatory lesions. Furthermore, it is known that mPGES-1 is involved in malignant tumors (for example, colon cancer, breast cancer, lung cancer, and prostate cancer) (see Non-Patent Literature 7, Non-Patent Literature 8, and Non-Patent Literature 9).

It is described in Patent Literature 1 that a heterocyclic derivative represented by General Formula [1] or a tautomer of the derivative or a pharmaceutically acceptable salt thereof has mPGES-1 inhibitory activity. Furthermore, in Patent Literatures 2 and 3, small molecules having mPGES-1 inhibitory activity are described. In Non-Patent Literature 10, it is described that CANEPHRON (registered trademark) N contains a plant-derived component and has mPGES-1 inhibitory activity.

However, nothing has been reported so far on the relationship between chronic prostatitis and the mPGES-1 pathway.

CITATION LIST

Patent Literature

Patent Literature 1: WO 2013/024898

Patent Literature 2: WO 2011/023812

Patent Literature 3: WO 2017/073709

Non-Patent Literature

Non-Patent Literature 1: JAMA. 1999 Jul. 21: 282(3): 236-7

Non-Patent Literature 2: Int. J. Urol. 2001 September; 8(9): 495-499

Non-Patent Literature 3: J. Urol. 2008 May: 179(5): 1857-1862

Non-Patent Literature 4: Jakobsson, et al., Proc. Natl. Acad. Sci. USA, 1999, 96, 7220-7225

Non-Patent Literature 5: Biochem. Biophys. Res. Commun., 2002, 291, 884-889

Non-Patent Literature 6: J. Biol. Chem., 2000, 275, 32775-32782

Non-Patent Literature 7: J. Biol. Chem., 2003, 278(21), 19396-19405

Non-Patent Literature 8: Oncogene, 2012, 31(24), 2943-2952

Non-Patent Literature 9: Cancer Res., 2008, 68(9), 3251-3259

Non-Patent Literature 10: j. phymed. 2019, 60, 152987

SUMMARY OF INVENTION

Technical Problem

An object to be achieved by the present invention is to provide a prophylactic and/or therapeutic agent for chronic prostatitis/chronic pelvic pain syndrome.

Solution to Problem

The inventors of the present invention set out to elucidate the pathophysiology of chronic prostatitis/chronic pelvic pain syndrome and found that the mPGES-1 pathway is involved in chronic prostatitis/chronic pelvic pain syndrome. Furthermore, the present inventors found that pain and inflammation of animal models of chronic prostatitis can be reduced by using an mPGES-1 inhibitor, thus completing the invention.

The invention relates to the following.

(1) A prophylactic and/or therapeutic agent for chronic prostatitis/chronic pelvic pain syndrome, the agent containing an mPGES-1 inhibitor as an active ingredient.

(2) The prophylactic and/or therapeutic agent for chronic prostatitis/chronic pelvic pain syndrome according to the above-described item (1), wherein the mPGES-1 inhibitor is a compound of Formula [1] (hereinafter, also referred to as present compound) or a tautomer of the compound, or a pharmaceutically acceptable salt thereof, and the compound of Formula [1] is as follows:

Formula [1]

[Chemical Formula 1]

[1]

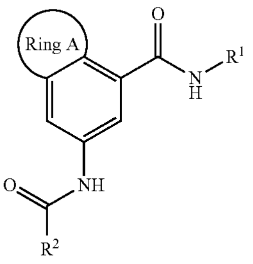

wherein ring A represents a group represented by Formula [2], [3], or [4]:

[Chemical Formula 2]

[2]

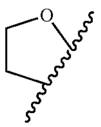

[3]

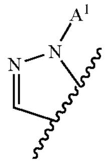

[4]

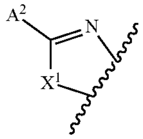

wherein $X^1$ represents NH, N-alkyl, or O;

$A^1$ represents hydrogen or alkyl;

$A^2$ represents:

i) hydrogen, ii) halogen, iii) alkyl which may be substituted with one to three groups selected from the group consisting of halogen, amino, monoalkylamino, dialkylamino, carbamoyl, monoalkylaminocarbonyl, dialkylaminocarbonyl, saturated cyclic aminocarbonyl, alkoxy, alkoxyalkoxy, and alkylcarbonyloxy, iv) cycloalkyl which may be substituted with alkyl, wherein said alkyl may be substituted with one to three halogens, v) alkoxy, vi) a saturated heterocyclic group which may be substituted with alkyl, alkyloxycarbonyl, alkylcarbonyl, or oxo, vii) alkylthio, viii) alkylsulfonvl, ix) alkylsulfinyl, x) Formula [5]:

[Chemical Formula 3]

[5]

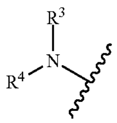

wherein $R^3$ and $R^4$ are identical or different and each represent:

a) hydrogen, b) alkyl which may be substituted with a group selected from the group consisting of monoalkylamino, dialkylamino, saturated cyclic amino optionally substituted with alkyl, a saturated heterocyclic group optionally substituted with alkyl, alkoxy, hydroxycarbonyl, hydroxyl, alkyloxycarbonyl, and alkylthio, or c) cycloalkyl, or xi) saturated cyclic amino which may be substituted with alkyl, amino, monoalkylamino, dialkylamino, alkoxy, or hydroxyl;

$R^1$ represents phenyl, benzyl, naphthyl, cycloalkyl, cycloalkylmethyl, heteroaryl, heteroarylmethyl, 1,2,3,4-tetrahydronaphthalen-5-yl, 1,2,3,4-tetrahydronaphthalen-6-yl, 2,3-dihydro-1H-inden-4-yl, 2,3-dihydro-1H-inden-5-yl, 1,2-dihydrocyclobutabenzen-3-yl, 1,2-dihydrocyclobutabenzen-4-yl, or alkyl, wherein said phenyl, benzyl, cycloalkyl, cycloalkylmethyl, heteroaryl, and heteroarylmethyl may be substituted with one to three groups selected from the group consisting of:

i) halogen, ii) alkyl which may be substituted with one to three groups selected from the group consisting of halogen, hydroxy, and phenyl, iii) alkoxy, iv) hydroxy, and v) cyano;

$R^2$ represents phenyl or pyridyl, wherein said phenyl and pyridyl may be substituted with one to three groups selected from the group consisting of:

i) halogen, ii) alkylsulfonyl, iii) alkoxy which may be substituted with one to three halogens or alkoxies, iv) alkynyl which may be substituted with alkoxyalkyl or cycloalkyl, and v) alkyl which may be substituted with one to three groups selected from the group consisting of alkoxy, alkoxyalkoxy, cycloalkyl, phenyl, and halogen.

(3) The prophylactic and/or therapeutic agent for chronic prostatitis/chronic pelvic pain syndrome according to the above-described item (2), wherein the ring A represents a group represented by Formula [4], and $X^1$ represents NH.

(4) The prophylactic and/or therapeutic agent for chronic prostatitis/chronic pelvic pain syndrome according to the above-described item (2) or (3), wherein $R^1$ represents phenyl, 1,2,3,4-tetrahydronaphthalen-5-yl, 1,2,3,4 tetrahydronaphthalen-6-yl, 2,3-dihydro-1H-inden-4-yl, 2,3-dihydro-1H-inden-5-yl, 1,2-dihydrocyclobutabenzen-3-yl, or 1,2-dihydrocyclobutabenzen-4-yl, wherein said phenyl may be substituted with one to three groups selected from the group consisting of:
i) halogen,
ii) alkyl which may be substituted with one to three halogens,
iii) alkoxy, and
iv) cyano.

(5) The prophylactic and/or therapeutic agent for chronic prostatitis/chronic pelvic pain syndrome according to any one of the above-described items (2) to (4), wherein $R^2$ represents phenyl, and
said phenyl may be substituted with one to three groups selected from the group consisting of:
i) halogen,
ii) alkylsulfonyl,
iii) alkoxy which may be substituted with alkoxy,
iv) alkynyl which may be substituted with alkoxyalkyl or cycloalkyl, and
v) alkyl which may be substituted with one to three groups selected from the group consisting of halogen, alkoxy, alkoxyalkoxy, cycloalkyl, and phenyl.

(6) The prophylactic and/or therapeutic agent for chronic prostatitis/chronic pelvic pain syndrome according to any one of the above-described items (2) to (5), wherein the ring A represents a group represented by General Formula [4];
$X^1$ represents NH;
$A^2$ represents:
i) hydrogen,
ii) alkyl which may be substituted with a group selected from the group consisting of halogen, monoalkylamino, dialkylamino, monoalkylaminocarbonyl, dialkylaminocarbonyl, saturated cyclic aminocarbonyl, alkoxy, alkoxyalkoxy, and alkylcarbonyloxy,
iii) cycloalkyl which may be substituted with alkyl optionally substituted with one to three halogens,
iv) alkoxy,
v) a saturated heterocyclic group which may be substituted with alkyl or alkyloxycarbonyl,
vi) alkylthio,
vii) alkylsulfonyl,
viii) alkylsulfinyl,
ix) amino substituted with alkyl which may be substituted with a group selected from the group consisting of monoalkylamino, dialkylamino, saturated cyclic amino optionally substituted with alkyl, tetrahydrofuryl, morpholino, alkoxy, hydroxycarbonyl, hydroxyl, and alkylthio,
x) amino substituted with cycloalkyl, or
xi) saturated cyclic amino which may be substituted with alkyl, dialkylamino, alkoxy, or hydroxyl;
$R^1$ represents:
i) phenyl which may be substituted with one to three groups selected from the group consisting of halogen, alkyl optionally substituted with one to three halogens, alkoxy, and cyano,
ii) 1,2,3,4-tetrahydronaphthalen-5-yl,
iii) 2,3-dihydro-1H-inden-5-yl,
iv) benzyl which may be substituted with halogen or with alkyl optionally substituted with one to three halogens,
v) cycloalkyl,
vi) cycloalkylmethyl,
vii) naphthyl,
viii) pyridylmethyl which may be substituted with alkyl optionally substituted with one to three halogens,
ix) thienyl,
x) thienylmethyl,
xi) benzothiazolyl,
xii) benzothiadiazolyl,
xiii) indolyl, or
xiv) alkyl; and
$R^2$ represents phenyl or pyridyl,
wherein said phenyl may be substituted with one to three groups selected from the group consisting of:
i) halogen,
ii) alkylsulfonyl,
iii) alkoxy which may be substituted with alkoxy,
iv) alkynyl which may be substituted with alkoxyalkyl or cycloalkyl, and
v) alkyl which may be substituted with one to three groups selected from the group consisting of halogen, alkoxy, alkoxyalkoxy, cycloalkyl, and phenyl, and
said pyridyl may be substituted with halogen.

(7) The prophylactic and/or therapeutic agent for chronic prostatitis/chronic pelvic pain syndrome according to any one of the above-described items (2) to (6), wherein the ring A represents a group represented by General Formula [4];
$X^1$ represents NH;
$A^2$ represents alkoxy-substituted alkyl, dialkylamino, tetrahydrofuryl, tetrahydrofurylmethyl, alkoxyalkylamino, or cycloalkyl which may be substituted with unsubstituted alkyl or alkyl substituted with one to three halogens;
$R^1$ represents phenyl substituted with one halogen and one methyl; and
$R^2$ represents phenyl which may be substituted with one trifluoromethyl or two halogens.

(8) The prophylactic and/or therapeutic agent for chronic prostatitis/chronic pelvic pain syndrome according to any one of the above-described items (2) to (7), wherein the mPGES-1 inhibitor is a compound selected from the group consisting of:
(1) N-[2-(trifluoromethyl)benzyl]-6-({[2-(trifluoromethyl)phenyl]carbonyl}amino)-1H-benzimidazole-4-carboxamide,
(2) N-cyclohexyl-6-({[2-(trifluoromethyl)phenyl]carbonyl}amino)-1H benzimidazole-4-carboxamide,
(3) N-(3-chloro-2-methyl phenyl)-6-({[2-(trifluoromethyl)phenyl]carbonyl}amino)-1H-benzimidazole-4-carboxamide,
(4) N-[(1-hydroxycyclohexyl)methyl]-6-({[2-(trifluoromethyl)phenyl]carbonyl}amino)-1H-benzimidazole-4-carboxamide,
(5) N-[2-(trifluoromethyl)benzyl]-5-({[2-(trifluoromethyl)phenyl]carbonyl}amino}-2,3-dihydro-1-benzofuran-7-carboxamide.
(6) N-cyclohexyl-5-({[2-(trifluoromethyl)phenyl]carbonyl}amino)-2,3-dihydro-1-benzofuran-7-carboxamide,
(7) N-(3-chloro-2-methylphenyl)-5-({[2-(trifluoromethyl)phenyl]carbonyl}amino)-2,3-dihydro-1-benzofuran-7-carboxamide,
(8) N-cyclohexyl-5-({[2-(trifluoromethyl)phenyl]carbonyl}amino)-1H-indazole-7-carboxamide,
(9) N-[2-(trifluoromethyl)benzyl]-5-({[2-(trifluoromethyl)phenyl]carbonyl}amino)-1H-indazole-7-carboxamide,
(10) N-(3-chloro-2-methylphenyl)-2-(methoxymethyl)-6-({[2-(trifluoromethyl)phenyl]carbonyl}amino)-1H-benzimidazole-4-carboxamide,

(11) 2-methyl-N-[2-(trifluoromethyl)benzyl]-6-({[2 (trifluoromethyl)phenyl]carbonyl}amino)-1H-benzimidazole-4-carboxamide,

(12) N-cyclohexyl-2-methyl-6-({[2-(trifluoromethyl)phenyl]carbonyl}amino)-1H-benzimidazole-4-carboxamide,

(13) N-(3-chloro-2-methylphenyl)-2-methyl-6-({[2-(trifluoromethyl)phenyl]carbonyl}amino)-1H-benzimidazole-4-carboxamide,

(14) N-cyclopentyl-2-methyl-6-({[2-(trifluoromethyl)phenyl]carbonyl}amino)-1H-benzimidazole-4-carboxamide,

(15) N-cyclobutyl-2-methyl-6-({[2-(trifluoromethyl)phenyl]carbonyl}amino)-1H-benzimidazole-4-carboxamide,

(16) N-(3-chloro-2-methylphenyl)-2-ethyl-6-({[2-(trifluoromethyl)phenyl]carbonyl}amino)-1H-benzimidazole-4-carboxamide,

(17) N-cyclohexyl-2-ethyl-6-({[2-(trifluoromethyl)phenyl]carbonyl}amino)-1H-benzimidazole-4-carboxamide.

(18) 2-ethyl-N-[2-(trifluoromethyl)benzyl]-6-({[2-(trifluoromethyl)phenyl]carbonyl}amino)-1H-benzimidazole-4-carboxamide,

(19) N-cyclohexyl-2-(methoxymethyl)-6-({[2-(trifluoromethyl)phenyl]carbonyl}amino)-1H-benzimidazole-4-carboxamide,

(20) 2-(methoxymethyl)-N-[2-(trifluoromethyl)benzyl]-6-({[2-(trifluoromethyl)phenyl]carbonyl}amino)-1H-benzimidazole-4-carboxamide,

(21) 2-(methoxymethyl)-N-(2-methylphenyl)-6-({[2 (trifluoromethyl)phenyl]carbonyl}amino)-1H-benzimidazole-4-carboxamide,

(22) 2-(methoxymethyl)-N-(4-methylphenyl)-6-({[2-(trifluoromethyl)phenyl]carbonyl}amino)-1H-benzimidazole-4-carboxamide,

(23) N-(2-chlorobenzyl)-2-(methoxymethyl)-6-({[2-(trifluoromethyl)phenyl]carbonyl}amino)-1H-benzimidazole-4-carboxamide,

(24) 2-(methoxymethyl)-N-(4-methylbenzyl)-6-({[2-(trifluoromethyl)phenyl]carbonyl}amino)-1H-benzimidazole-4-carboxamide,

(25) N-(4,4-difluorocyclohexyl)-2-(methoxymethyl)-6-({[2 (trifluoromethyl)phenyl]carbonyl}amino)-1H-benzimidazole-4-carboxamide,

(26) N-(4-tert-butylphenyl)-2-(methoxymethyl)-6-({[2-(trifluoromethyl)phenyl]carbonyl}amino)-1H-benzimidazole-4-carboxamide,

(27) 2-(methoxymethyl)-N-[4-(trifluoromethyl)phenyl]-6-({[2-(trifluoromethyl)phenyl]carbonyl}amino)-1H-benzimidazole-4-carboxamide,

(28) N-(2,4-dimethylphenyl)-2-(methoxymethyl)-6-({[2-(trifluoromethyl)phenyl]carbonyl}amino)-1H-benzimidazole-4-carboxamide,

(29) N-(2-chloro-4-methyl phenyl)-2-(methoxymethyl)-6-({[2-(trifluoromethyl)phenyl]carbonyl}amino)-1H-benzimidazole-4-carboxamide,

(30) N-(3,4-dimethylphenyl)-2-(methoxymethyl)-6-({[2 (trifluoromethyl)phenyl]carbonyl}amino)-1H-benzimidazole-4-carboxamide,

(31) N-(3-chloro-4-methylphenyl)-2-(methoxymethyl)-6-({[2-(trifluoromethyl)phenyl]carbonyl}amino)-1H-benzimidazole-4-carboxamide,

(32) N-(2,3-dihydro-1H-inden-5-yl)-2-(methoxymethyl)-6-({[2-(trifluoromethyl)phenyl]carbonyl}amino)-1H-benzimidazole-4-carboxamide,

(33) 2-(methoxymethyl)-N-(5,6,7,8-tetrahydronaphthalen-1-yl)-6-({[2-(trifluoromethyl)phenyl]carbonyl}amino)-1H-benzimidazole-4-carboxamide,

(34) N-(2-fluorophenyl)-2-(methoxymethyl)-6-({[2-(trifluoromethyl)phenyl]carbonyl}amino)-1H-benzimidazole-4-carboxamide,

(35) 2-(methoxymethyl)-N-(2-methoxyphenyl)-6-({[2-(trifluoromethyl)phenyl]carbonyl}amino)-1H-benzimidazole-4-carboxamide,

(36) 2-(methoxymethyl)-N-(4-methoxyphenyl)-6-({[2-(trifluoromethyl)phenyl]carbonyl}amino)-1H-benzimidazole-4-carboxamide,

(37) N-(3-bromo-2-methylphenyl)-2-(methoxymethyl)-6-({[2-(trifluoromethyl)phenyl]carbonyl}amino)-1H-benzimidazole-4-carboxamide,

(38) N-(3-chloro-2-methylbenzyl)-2-(methoxymethyl)-6-({[2-(trifluoromethyl)phenyl]carbonyl}amino)-1H-benzimidazole-4-carboxamide,

(39) N-(2,6-difluorophenyl)-2-(methoxymethyl)-6-({[2-(trifluoromethyl)phenyl]carbonyl}amino)-1H-benzimidazole-4-carboxamide,

(40) N-(3-cyano-2-methylphenyl)-2-(methoxymethyl)-6-({[2-(trifluoromethyl)phenyl]carbonyl}amino)-1H-benzimidazole-4-carboxamide,

(41) 2-(methoxymethyl)-6-({[2-(trifluoromethyl)phenyl]carbonyl}amino)-N-([3-(trifluoromethyl)pyridin-2-yl]methyl)-1H-benzimidazole-4-carboxamide,

(42) N-(2-chloro-6-methyl phenyl)-2-(methoxymethyl)-6-({[2-(trifluoromethyl)phenyl]carbonyl}amino)-1H-benzimidazole-4-carboxamide,

(43) 2-(2-amino-2-oxoethyl)-N-(3-chloro-2-methylphenyl)-6-({[2-(trifluoromethyl)phenyl]carbonyl}amino)-1H-benzimidazole-4-carboxamide,

(44) 2-(2-amino-2-oxoethyl)-N-[2-(trifluoromethyl)benzyl]-6-({[2-(trifluoromethyl)phenyl]carbonyl}amino)-1H-benzimidazole-4-carboxamide,

(45) N-(3-chloro-2-methylphenyl)-1-methyl-6-({[2-(trifluoromethyl)phenyl]carbonyl}amino)-1H-benzimidazole-4-carboxamide,

(46) N-cyclohexyl-1-methyl-6-({[2-(trifluoromethyl)phenyl]carbonyl}amino)-1H-benzimidazole-4-carboxamide,

(47) 1-methyl-N-[2-(trifluoromethyl)benzyl]-6-({[2-(trifluoromethyl)phenyl]carbonyl}amino)-1H-benzimidazole-4-carboxamide,

(48) N-(3-chloro-2-methylphenyl)-1-ethyl-6-({[2-(trifluoromethyl)phenyl]carbonyl}amino)-1H-benzimidazole-4-carboxamide,

(49) N-cyclohexyl-1-ethyl-6-({[2-(trifluoromethyl)phenyl]carbonyl}amino)-1H benzimidazole-4-carboxamide,

(50) 1-ethyl-N-[2-(trifluoromethyl)benzyl]-6-({[2-(trifluoromethyl)phenyl]carbonyl}amino)-1H-benzimidazole-4-carboxamide,

(51) N-(3-chloro-2-methylphenyl)-2-methyl-6-({[2-(trifluoromethyl)phenyl]carbonyl}amino)-1,3-benzoxazole-4-carboxamide,

(52) 2-methyl-N-[2-(trifluoromethyl)benzyl]-6-({[2-(trifluoromethyl)phenyl]carbonyl}amino)-1,3-benzoxazole-4-carboxamide,

(53) N-(3-chloro-2-methylphenyl)-2-ethyl-6-({[2-(trifluoromethyl)phenyl]carbonyl}amino)-1,3-benzoxazole-4-carboxamide,

(54) N-(3-chloro-2-methylphenyl)-2-ethoxy-6-({[2 (trifluoromethyl)phenyl]carbonyl}amino)-1H-benzimidazole-4-carboxamide,

(55) 2-ethoxy-N-[2-(trifluoromethyl)benzyl]-6-({[2-(trifluoromethyl)phenyl]carbonyl}amino)-1H-benzimidazole-4-carboxamide,

(56) N-(3-chloro-2-methyl phenyl)-2-(1-chloro-2-methylpropan-2-yl)-6-({[2-(trifluoromethyl)phenyl]carbonyl}amino)-1H-benzimidazole-4-carboxamide,

(57) N-(3-chloro-2-methylphenyl)-2-[(di methyl amino) methyl]-6-({[2-(trifluoromethyl)phenyl] carbonyl}amino)-1H-benzimidazole-4-carboxamide,
(58) N-(3-chloro-2-methylphenyl)-2-(2-methylpropyl)-6-({[2 (trifluoromethyl)phenyl]carbonyl}amino)-1H-benzimidazole-4-carboxamide,
(59) 2-(2-methylpropyl)-N-[2-(trifluoromethyl)benzyl]-6-({[2-(trifluoromethyl)phenyl]carbonyl}amino)-1H-benzimidazole-4-carboxamide,
(60) tert-butyl 3-{4-[(3-chloro-2-methylphenyl)carbamoyl]-6-({[2-(trifluoromethyl)phenyl]carbonyl}amino)-1H-benzimidazol-2-yl}azetidine-1-carboxylate,
(61) N-(3-chloro-2-methylphenyl)-2-[(methylamino) methyl]-6-({[2-(trifluoromethyl)phenyl] carbonyl}amino)-1H-benzimidazole-4-carboxamide,
(62){4-[(3-chloro-2-methylphenyl)carbamoyl]-6-({[2-(trifluoromethyl)phenyl]carbonyl}amino)-1H-benzimidazol-2-yl}methyl acetate.
(63) N-(3-chloro-2-methylphenyl)-2-[(2R)-tetrahydrofuran-2-yl]-6-({[2 (trifluoromethyl)phenyl]carbonyl}amino)-1H-benzimidazole-4-carboxamide,
(64) 2-[(2R)-tetrahydrofuran-2-yl]-N-[2-(trifluoromethyl) benzyl]-6-({[2-(trifluoromethyl)phenyl] carbonyl}amino)-1H-benzimidazole-4-carboxamide,
(65) N-(3-chloro-2-methylphenyl)-2-[(2S)-tetrahydrofuran-2-yl]-6-({[2-(trifluoromethyl)phenyl]carbonyl}amino)-1H-benzimidazole-4-carboxamide,
(66) 2-[(2S)-tetrahydrofuran-2-yl]-N-[2-(trifluoromethyl) benzyl]-6-({[2-(trifluoromethyl)phenyl] carbonyl}amino)-1H-benzimidazole-4-carboxamide,
(67) 2-(1-acetylazetidin-3-yl)-N-(3-chloro-2-methylphenyl)-6-({[2-(trifluoromethyl)phenyl]carbonyl}amino)-1H-benzimidazole-4-carboxamide,
(68) tert-butyl (2S)-2-(4-[(3-chloro-2-methylphenyl)carbamoyl]-6-({[2-(trifluoromethyl)phenyl] carbonyl}amino)-1H-benzimidazol-2-yl}pyrrolidine-1-carboxylate,
(69) tert-butyl (2R)-2-{4-[(3-chloro-2-methylphenyl)carbamoyl]-6-({[2-(trifluoromethyl)phenyl] carbonyl}amino)-1H-benzimidazol-2-yl}pyrrolidine-1-carboxylate,
(70) N-(3-chloro-2-methylphenyl)-2-[(2S)-pyrrolidin-2-yl]-6-({[2-(trifluoromethyl)phenyl]carbonyl}amino)-1H-benzimidazole-4-carboxamide,
(71) N-(3-chloro-2-methylphenyl)-2-[(2S)-1-methylpyrrolidin-2-yl]-6-({[2-(trifluoromethyl)phenyl] carbonyl}amino)-1H-benzimidazole-4-carboxamide,
(72) 2-[(2S)-1-acetylpyrrolidin-2-yl]-N-(3-chloro-2-methylphenyl)-6-({[2-(trifluoromethyl)phenyl] carbonyl}amino)-1H-benzimidazole-4-carboxamide,
(73) N-(3-chloro-2-methylphenyl)-2-[(2-methoxyethoxy) methyl]-6-({[2-(trifluoromethyl)phenyl] carbonyl}amino)-1H-benzimidazole-4-carboxamide,
(74) N-(3-chloro-2-methylphenyl)-2-(1-methoxy-2-methylpropan-2-yl)-6-({[2-(trifluoromethyl)phenyl] carbonyl}amino)-1H-benzimidazole-4-carboxamide,
(75) 2-tert-butyl-N-(3-chloro-2-methylphenyl)-6-({[2-(trifluoromethyl)phenyl]carbonyl}amino)-1H-benzimidazole-4-carboxamide,
(76) 2-tert-butyl-6-({[2-(trifluoromethyl)phenyl] carbonyl}amino)-N-{[3-(trifluoromethyl)pyridin-2-yl] methyl}-1H-benzimidazole-4-carboxamide,
(77) N-(3-chloro-2-methylphenyl)-2-(2-ethoxyethyl)-6-({[2 (trifluoromethyl)phenyl]carbonyl}amino)-1H-benzimidazole-4-carboxamide,
(78) N-(3-chloro-2-methylphenyl)-2-(ethoxymethyl)-6-({[2-(trifluoromethyl)phenyl]carbonyl}amino)-1H-benzimidazole-4-carboxamide,
(79) 2-(ethoxymethyl)-6-({[2-(trifluoromethyl)phenyl] carbonyl}amino)-N-{[3-(trifluoromethyl)pyridin-2-yl] methyl}-1H-benzimidazole-4-carboxamide,
(80) N-(3-chloro-2-methylphenyl)-2-(2-methoxyethyl)-6-({[2-(trifluoromethyl)phenyl]carbonyl}amino)-1H-benzimidazole-4-carboxamide,
(81) N-(3-chloro-2-methylphenyl)-2-(2,2-dimethylpropyl)-6-({[2-(trifluoromethyl)phenyl]carbonyl}amino)-1H-benzimidazole-4-carboxamide,
(82) N-(3-chloro-2-methyl phenyl)-2-cyclopropyl-6-({[2-(trifluoromethyl)phenyl]carbonyl}amino)-1H-benzimidazole-4-carboxamide,
(83) N-(3-chloro-2-methylphenyl)-2-(2-methylpentan-2-yl)-6-({[2-(trifluoromethyl)phenyl]carbonyl}amino)-1H-benzimidazole-4-carboxamide,
(84) N-(3-chloro-2-methylphenyl)-2-(1-methylcyclopropyl)-6-({[2-(trifluoromethyl)phenyl]carbonyl}amino)-1H-benzimidazole-4-carboxamide,
(85) 2-tert-butyl-N-(3-chloro-4-methylphenyl)-6-({[2-(trifluoromethyl)phenyl]carbonyl}amino)-1H-benzimidazole-4-carboxamide,
(86) 2-tert-butyl-N-(3-chloro-2-methylphenyl)-6-({[2,5-dichlorophenyl)carbonyl]amino}-1H-benzimidazole-4-carboxamide,
(87) 2-tert-butyl-N-(3-chloro-4-methylphenyl)-6-({[2,5-dichlorophenyl)carbonyl]amino}-1H-benzimidazole-4-carboxamide,
(88) N-(3-chloro-2-methylphenyl)-2-[1-(trifluoromethyl) cyclopropyl]-6-({[2-(trifluoromethyl)phenyl] carbonyl}amino)-1H-benzimidazole-4-carboxamide,
(89) N-(3-chloro-2-methylphenyl)-2-(methoxymethyl)-1-methyl-6-({[2-(trifluoromethyl)phenyl]carbonyl}amino)-1H-benzimidazole-4-carboxamide,
(90) N-(2-chlorobenzyl)-2-(methoxymethyl)-1-methyl-6-({[2-(trifluoromethyl)phenyl]carbonyl}amino)-1H-benzimidazole-4-carboxamide,
(91) 6-{[(2-chloro-6-fluorophenyl)carbonyl]amino}-N-(3-chloro-2-methylphenyl)-2-(methoxymethyl)-1H-benzimidazole-4-carboxamide,
(92) 6-{[(2-chloro-4-fluorophenyl)carbonyl]amino}-N-(3-chloro-2-methylphenyl)-2-methoxymethyl-1H-benzimidazole-4-carboxamide,
(93) 6-{[(2-chloro-5-fluorophenyl)carbonyl]amino}-N-(3-chloro-2-methylphenyl)-2-(methoxymethyl)-1H-benzimidazole-4-carboxamide,
(94) N-(3-chloro-2-methylphenyl)-6-{[(2-chlorophenyl)carbonyl]amino}-2-(methoxy methyl)-1H-benzimidazole-4-carboxamide,
(95) N-(3-chloro-2-methylphenyl)-6-{[(2-chloropyridin-3-yl)carbonyl]amino}-2-(methoxymethyl)-1H-benzimidazole-4-carboxamide,
(96) 6-{[(2-bromophenyl)carbonyl]amino}-N-(3-chloro-2-methylphenyl)-2-(methoxymethyl)-1H-benzimidazole-4-carboxamide,
(97) N-(3-chloro-2-methylphenyl)-6-{[(2,6-dichlorophenyl) carbonyl]amino}-2-(methoxymethyl)-1H-benzimidazole-4-carboxamide,
(98) N-(3-chloro-2-methylphenyl)-6-{[(2,5-dichlorophenyl) carbonyl]amino}-2-(methoxymethyl)-1H-benzimidazole-4-carboxamide,
(99) 6-{[(2-chloro-3-fluorophenyl)carbonyl]amino}-N-(3-chloro-2-methylphenyl)-2-(methoxymethyl)-1H-benzimidazole-4-carboxamide, (100) 6-{[(2-chloro-3,6-difluorophenyl)carbonyl]amino}-N-(3-chloro-2-methylphenyl)-2-(methoxymethyl)-1H-benzimidazole-4-carboxamide,
(101) 6-{[(2-bromo-6-chlorophenyl)carbonyl]amino}-N-(3-chloro-2-methylphenyl)-2-(methoxymethyl)-1H-benzimidazole-4-carboxamide,
(102) 6-{[(2-bromo-6-fluorophenyl)carbonyl]amino}-N-(3-chloro-2-methylphenyl)-2-(methoxymethyl)-1H-benzimidazole-4-carboxamide,
(103) N-(3-chloro-2-methylphenyl)-6-{[(2-chloro-6-methylphenyl)carbonyl]amino}-2-(methoxymethyl)-1H-benzimidazole-4-carboxamide,
(104) N-(3-chloro-2-methylphenyl)-6-{[(2-chloro-4-methylphenyl)carbonyl]amino}-2-(methoxymethyl)-1H-benzimidazole-4-carboxamide,
(105) 6-{[(5-bromo-2-chlorophenyl)carbonyl]amino}-N-(3-chloro-2-methylphenyl)-2-(methoxymethyl)-1H-benzimidazole-4-carboxamide,
(106) 6-{[(2-bromo-5-chlorophenyl)carbonyl]amino}-N-(3-chloro-2-methylphenyl)-2-(methoxymethyl)-1H-benzimidazole-4-carboxamide,
(107) N-(3-chloro-2-methylphenyl)-6-{[(2-chloro-5-methylphenyl)carbonyl]amino}-2-(methoxymethyl)-1H-benzimidazole-4-carboxamide,
(108) N-(3-chloro-2-methylphenyl)-2-(methoxymethyl)-6-({[5-methyl-2-(trifluoromethyl)phenyl]carbonyl}amino)-1H-benzimidazole-4-carboxamide,
(109) 6-({[2,5-bis(trifluoromethyl)phenyl]carbonyl}amino)-N-(3-chloro-2-methylphenyl)-2-(methoxymethyl)-1H-benzimidazole-4-carboxamide,
(110) 6-({[2,4-bis(trifluoromethyl)phenyl]carbonyl}amino)-N-(3-chloro-2-methylphenyl)-2-(methoxymethyl)-1H-benzimidazole-4-carboxamide,
(111) N-(3-chloro-2-methylphenyl)-6-({[5-fluoro-2-(trifluoromethyl)phenyl]carbonyl}amino)-2-(methoxymethyl)-1H-benzimidazole-4-carboxamide,
(112) N-(3-chloro-2-methylphenyl)-6-({[2-chloro-6-(trifluoromethyl)phenyl]carbonyl}amino)-2-(methoxymethyl)-1H-benzimidazole-4-carboxamide,
(113) N-(3-chloro-2-methylphenyl)-6-[({2-chloro-5-[2-(propan-2-yloxy)ethoxy]phenyl}carbonyl)amino]-2-(methoxymethyl)-1H-benzimidazole-4-carboxamide,
(114) 6-({[2-chloro-5-(2-ethoxyethoxy)phenyl]carbonyl}amino)-N-(3-chloro-2-methylphenyl)-2-(methoxymethyl)-1H-benzimidazole-4-carboxamide,
(115) 6-({[2-chloro-5-(3-methoxypropyl)phenyl]carbonyl}amino)-N-(3-chloro-2-methylphenyl)-2-(methoxymethyl)-1H-benzimidazole-4-carboxamide,
(116) 6-({[5-(3-tert-butoxyprop-1-yn-1-yl)-2-chlorophenyl]carbonyl}amino)-N-(3 chloro-2-methylphenyl)-2-(methoxymethyl)-1H-benzimidazole-4-carboxamide,
(117) 6-({[5-(3-tert-butoxypropyl)-2-chlorophenyl]carbonyl}amino)-N-(3-chloro-2-methylphenyl)-2-(methoxymethyl)-1H-benzimidazole-4-carboxamide,
(118) 6-({[2-chloro-5-(3-hydroxy-3-methylbutyl)phenyl]carbonyl}amino)-N-(3-chloro-2-methylphenyl)-2-(methoxymethyl)-1H-benzimidazole-4-carboxamide,
(119) 6-({[2-chloro-5-(ethoxymethyl)phenyl]carbonyl}amino)-N-(3-chloro-2-methylphenyl)-2-(methoxymethyl)-1H-benzimidazole-4-carboxamide,
(120) 6-[({2-chloro-5-[(2-ethoxyethoxy)methyl]phenyl}carbonyl)amino]-N-(3-chloro-2-methylphenyl)-2-(methoxymethyl)-1H-benzimidazole-4-carboxamide,
(121) 6-({[2-chloro-5-(2-cyclopropylethyl)phenyl]carbonyl}amino)-N-(3-chloro-2-methylphenyl)-2-(methoxymethyl)-1H-benzimidazole-4-carboxamide,
(122) N-(3-chloro-2-methylphenyl)-6-({[2-chloro-5-(2-phenylethyl)phenyl]carbonyl}amino)-2-(methoxymethyl)-1H-benzimidazole-4-carboxamide,
(123) N-(3-chloro-2-methylphenyl)-2-cyclopentyl-6-({[2-(trifluoromethyl)phenyl]carbonyl}amino)-1H-benzimidazole-4-carboxamide,
(124) N-(3-chloro-2-methylphenyl)-2-cyclopentyl-6-{[(2,5-dichlorophenyl)carbonyl]amino}-1H-benzimidazole-4-carboxamide,
(125) 6-{[(2-chloro-6-fluorophenyl)carbonyl]amino}-N-(3-chloro-2-methylphenyl)-2-cyclopentyl-1H-benzimidazole-4-carboxamide,
(126) 6-{[(2-chloro-6-fluorophenyl)carbonyl]amino}-N-(3-chloro-2-methylphenyl)-2-[(2R)-tetrahydrofuran-2-yl]-1H-benzimidazole-4-carboxamide,
(127) N-(3-chloro-2-methylphenyl)-6-{[(2,6-dichlorophenyl)carbonyl]amino}-2-[(2R)-tetrahydrofuran-2-yl]-1H-benzimidazole-4-carboxamide,
(128) N-(3-chloro-2-methylphenyl)-6-{[(2,5-dichlorophenyl)carbonyl]amino}-2[(2R)-tetrahydrofuran-2-yl]-1H-benzimidazole-4-carboxamide,
(129) N-(3-chloro-2-methylphenyl)-2-[(2S)-5-oxopyrrolidin-2-yl]-6-({[2-(trifluoromethyl)phenyl]carbonyl}amino)-1H-benzimidazole-4-carboxamide,
(130) N-(3-chloro-2-methylphenyl)-2-[(2R)-5-oxopyrrolidin-2-yl]-6-({[2 (trifluoromethyl)phenyl]carbonyl}amino)-1H-benzimidazole-4-carboxamide,
(131) N-(3-chloro-2-methylphenyl)-2-[2-oxo-2-(pyrrolidin-1-yl)ethyl]-6-({[2-(trifluoromethyl)phenyl]carbonyl}amino)-1H-benzimidazole-4-carboxamide,
(132) N-(3-chloro-2-methylphenyl)-2-[2-(dimethylamino)-2-oxoethyl]-6-({[2-(trifluoromethyl)phenyl]carbonyl}amino)-1H-benzimidazole-4-carboxamide,
(133) N-(3-chloro-2-methylphenyl)-2-[2-(methylamino)-2-oxoethyl]-6-({[2-(trifluoromethyl)phenyl]carbonyl}amino)-1H-benzimidazole-4-carboxamide,
(134) 2-chloro-N-(3-chloro-2-methylphenyl)-6-({[2-(trifluoromethyl)phenyl]carbonyl}amino)-1H-benzimidazole-4-carboxamide,
(135) N-(3-chloro-2-methylphenyl)-2-[(2-methoxyethyl)amino]-6-({[2 (trifluoromethyl)phenyl]carbonyl}amino)-1H-benzimidazole-4-carboxamide,
(136) N-(3-chloro-2-methylphenyl)-2-({[2-hydroxyethyl)amino](trifluoromethyl)phenyl]carbonyl}amino)-1H-benzimidazole-4-carboxamide,
(137) N-(3-chloro-2-methylphenyl)-2-(methylamino)-6-({[2-(trifluoromethyl)phenyl]carbonyl}amino)-1H-benzimidazole-4-carboxamide,
(138) N-(3-chloro-2-methylphenyl)-2-(ethylamino)-6-({[2-(trifluoromethyl)phenyl]carbonyl}amino)-1H-benzimidazole-4-carboxamide,
(139) N-(3-chloro-2-methylphenyl)-2-[(2,2-dimethylpropyl)amino]-6-({[2 (trifluoromethyl)phenyl]carbonyl}amino)-1H-benzimidazole-4-carboxamide,
(140) N-(3-chloro-2-methylphenyl)-2-(cyclopentylamino)-6-({[2-(trifluoromethyl)phenyl]carbonyl}amino)-1H-benzimidazole-4-carboxamide,
(141) N-(3-chloro-2-methylphenyl)-2-(piperidin-1-yl)-6-({[2-(trifluoromethyl)phenyl]carbonyl}amino)-1H-benzimidazole-4-carboxamide,
(142) N-(3-chloro-2-methylphenyl)-2-(4-methylpiperazin-1-yl)-6-({[2-(trifluoromethyl)phenyl]carbonyl}amino)-1H-benzimidazole-4-carboxamide,
(143) 2-[bis(2-hydroxyethyl)amino]-N-(3-chloro-2-methylphenyl)-6-({[2-(trifluoromethyl)phenyl]carbonyl}amino)-1H-benzimidazole-4-carboxamide, (144) N-(3-chloro-2-methylphenyl)-2-(dimethylamino)-6-({[2 (trifluoromethyl)phenyl]carbonyl}amino)-1H-benzimidazole-4-carboxamide, (145) N-(3-chloro-2-methylphenyl)-2-{[2-(morpholin-4-yl)ethyl]amino}-6-({[2-(trifluoromethyl)phenyl]carbonyl}amino)-1H-benzimidazole-4-carboxamide, (146) N-(3-chloro-2-methylphenyl)-2-{[2-(dimethylamino)ethyl]amino}-6-({[2-(trifluoromethyl)phenyl]carbonyl}amino)-1H-benzimidazole-4-carboxamide, (147) N-(3-chloro-2-methylphenyl)-2-(3-hydroxyazetidine-1-yl)-6-({[2-(trifluoromethyl)phenyl]carbonyl}amino)-1H-benzimidazole-4-carboxamide, (148) N-(3-chloro-2-methylphenyl)-2-[(3S)-3-(dimethylamino)pyrrolidin-1-yl]-6-({[2-(trifluoromethyl)phenyl]carbonyl}amino)-1H-benzimidazole-4-carboxamide, (149) N-(3-chloro-2-methylphenyl)-2-[(3S)-3-hydroxypyrrolidin-1-yl]-6-({[2-(trifluoromethyl)phenyl]carbonyl}amino)-1H-benzimidazole-4-carboxamide, (150) N-(3-chloro-2-methylphenyl)-2-{[2-(diethylamino)ethyl]amino}-6-({[2-(trifluoromethyl)phenyl]carbonyl}amino)-1H-benzimidazole-4-carboxamide, (151) N-(3-chloro-2-methylphenyl)-2-{[2-(pyrrolidin-1-yl)ethyl]amino}-6-({[2-(trifluoromethyl)phenyl]carbonyl}amino)-1H-benzimidazole-4-carboxamide, (152) N-(3-chloro-2-methylphenyl)-2-{[3-(dimethylamino)propyl]amino}-6-({[2-(trifluoromethyl)phenyl]carbonyl}amino)-1H-benzimidazole-4-carboxamide, (153) N-(3-chloro-2-methylphenyl)-2-{[3-(dimethylamino)-2,2-dimethylpropyl]amino}-6-({[2-(trifluoromethyl)phenyl]carbonyl}amino)-1H-benzimidazole-4-carboxamide, (154) N-(3-chloro-2-methylphenyl)-2-{[2-(dipropan-2-ylamino)ethyl]amino}-6-({[2-(trifluoromethyl)phenyl]carbonyl}amino)-1H-benzimidazole-4-carboxamide, (155) N-(3-chloro-2-methylphenyl)-2-(morpholin-4-yl)-6-({[2-(trifluoromethyl)phenyl]carbonyl}amino)-1H-benzimidazole-4-carboxamide, (156) 2-amino-N-(3-chloro-2-methylphenyl)-6-({[2-(trifluoromethyl)phenyl]carbonyl}amino)-1H-benzimidazole-4-carboxamide, (157) N-(3-chloro-2-methylphenyl)-2-[(3-hydroxy-2,2-dimethylpropyl)amino]-6-({[2-(trifluoromethyl)phenyl]carbonyl}amino)-1H-benzimidazole-4-carboxamide, (158) N-(3-chloro-2-methylphenyl)-2-{[(3-methyloxetan-3-yl)methyl]amino}-6-({[2-(trifluoromethyl)phenyl]carbonyl}amino)-1H-benzimidazole-4-carboxamide, (159) tert-butyl N-{4-[(3-chloro-2-methylphenyl)carbamoyl]-6-({[2-(trifluoromethyl)phenyl]carbonyl}amino)-1H-benzimidazol-2-yl}glycinate, (160) N-{4-[(3-chloro-2-methylphenyl)carbamoyl]-6-({[2-(trifluoromethyl)phenyl]carbonyl}amino)-1H-benzimidazol-2-yl}glycine, (161) N-(3-chloro-2-methylphenyl)-2-[(3-hydroxy-2,2-dimethylpropyl)amino]-1-methyl-6-({[2-(trifluoromethyl)phenyl]carbonyl}amino)-1H-benzimidazole-4-carboxamide, (162) N-(3-chloro-2-methylphenyl)-2-[(3-methoxy-2,2-dimethylpropyl)amino]-6-({[2-(trifluoromethyl)phenyl]carbonyl}amino)-1H-benzimidazole-4-carboxamide, (163) N-(3-chloro-2-methylphenyl)-2-(pyrrolidin-1-yl)-6-({[2-(trifluoromethyl)phenyl]carbonyl}amino)-1H-benzimidazole-4-carboxamide, (164) 2-(azetidin-1-yl)-N-(3-chloro-2-methylphenyl)-6-({[2-(trifluoromethyl)phenyl]carbonyl}amino)-1H-benzimidazole-4-carboxamide, (165) N-(3-chloro-2-methylphenyl)-2-(3-methoxyazetidin-1-yl)-6-({[2-(trifluoromethyl)phenyl]carbonyl}amino)-1H-benzimidazole-4-carboxamide, (166) N-(3-chloro-2-methylphenyl)-2-[(2-hydroxy-2-methylpropyl)amino]-6-({[2-(trifluoromethyl)phenyl]carbonyl}amino)-1H-benzimidazole-4-carboxamide, (167) N-(3-chloro-2-methylphenyl)-2-{[(2S)-tetrahydrofuran-2-ylmethyl]amino}-6-({[2-(trifluoromethyl)phenyl]carbonyl}amino)-1H-benzimidazole-4-carboxamide, (168) N-(3-chloro-2-methylphenyl)-2-{[(2R)-tetrahydrofuran-2-ylmethyl]amino}-6-({[2-(trifluoromethyl)phenyl]carbonyl}amino)-1H-benzimidazole-4-carboxamide, (169) N-(3-chloro-2-methylphenyl)-2-{[(2S)-1-hydroxy-3-methylbutan-2-yl]amino}-6-({[2-(trifluoromethyl)phenyl]carbonyl}amino)-1H-benzimidazole-4-carboxamide, (170) N-(3-chloro-2-methylphenyl)-2-{[(2R)-1-hydroxy-3-methylbutan-2-yl]amino}-6-({[2-(trifluoromethyl)phenyl]carbonyl}amino)-1H-benzimidazole-4-carboxamide, (171) N-(3-chloro-2-methylphenyl)-2-{[(2S)-1-hydroxy-3,3-dimethyl butan-2-yl]amino}-6-({[2-(trifluoromethyl)phenyl]carbonyl}amino)-1H-benzimidazole-4-carboxamide, (172) N-(3-chloro-2-methylphenyl)-2-[(3-methoxy-2,2-dimethylpropyl)(methyl)amino]-6-({[2-(trifluoromethyl)phenyl]carbonyl}amino)-1H benzimidazole-4-carboxamide, (173) N-(3-chloro-2-methylphenyl)-2-[(3-methoxypropyl)amino]-6-({[2-(trifluoromethyl)phenyl]carbonyl}amino)-1H-benzimidazole-4-carboxamide, (174) N-(3-chloro-2-methylphenyl)-2-{[2-(propan-2-yloxy)ethyl]amino}-6-({[2-(trifluoromethyl)phenyl]carbonyl}amino)-1H-benzimidazole-4-carboxamide, (175) 2-[(2-tert-butoxyethyl)amino]-N-(3-chloro-2-methylphenyl)-6-({[2-(trifluoromethyl)phenyl]carbonyl}amino)-1H-benzimidazole-4-carboxamide, (176) N-(3-chloro-2-methylphenyl)-2-[(2-methoxy-2-methylpropyl)amino]-6-({[2-(trifluoromethyl)phenyl]carbonyl}amino)-1H-benzimidazole-4-carboxamide, (177) N-(3-chloro-2-methylphenyl)-2-{[2-(methylsulfanyl)ethyl]amino}-6-({[2 (trifluoromethyl)phenyl]carbonyl}amino)-1H-benzimidazole-4-carboxamide, (178) N-(3-chloro-2-methylphenyl)-2-(methylsulfanyl)-6-({[2-(trifluoromethyl)phenyl]carbonyl}amino)-1H-benzimidazole-4-carboxamide, (179) N-(3-chloro-2-methylphenyl)-2-(methylsulfonyl)-6-({[2-(trifluoromethyl)phenyl]carbonyl}amino)-1H-benzimidazole-4-carboxamide, (180) N-(3-chloro-2-methylphenyl)-2-(methylsulfinyl)-6-({[2-(trifluoromethyl)phenyl]carbonyl}amino)-1H-benzimidazole-4-carboxamide, (181) 6-{[(2-chloro-6-fluorophenyl)carbonyl]amino}-N-(3-chloro-2-methylphenyl)-2-(dimethylamino)-1H-benzimidazole-4-carboxamide, (182) N-(3-chloro-2-methylphenyl)-6-{[(2,6-dichlorophenyl)carbonyl]amino}-2-(dimethylamino)-1H-benzimidazole-4-carboxamide, (183) N-(3-chloro-2-methylphenyl)-6-{[(2,4-dichlorophenyl)carbonyl]amino}-2-(dimethylamino)-1H-benzimidazole-4-carboxamide.

(184) N-(3-chloro-2-methyl phenyl)-6-{[(2,5-dichlorophenyl)carbonyl]amino}-2-(dimethylamino)-1H-benzimidazole-4-carboxamide, (185) 6-{[(2-bromo-6-fluorophenyl)carbonyl]amino}-N-(3-chloro-2-methylphenyl)-2-(dimethylamino)-1H-benzimidazole-4-carboxamide, (186) 6-{[(2-bromo-6-chlorophenyl)carbonyl]amino}-N-(3-chloro-2-methylphenyl)-2-(dimethyl amino)-1H-benzimidazole-4-carboxamide, (187) 6-({[2-chloro-5-(cyclopropylethynyl)phenyl]carbonyl}amino)-N-(3-chloro-2-methylphenyl)-2-(dimethylamino)-1H-benzimidazole-4-carboxamide, (188) N-(3-chloro-2-methylphenyl)-6-{[(2,5-dichlorophenyl)carbonyl]amino}-2-[(3-hydroxy-2,2-dimethyl propyl)amino]-1H-benzimidazole-4-carboxamide, (189) N-(3-chloro-2-methylphenyl)-6-{[(2,5-dichlorophenyl)carbonyl]amino}-2-[(3-methoxy-2,2-dimethylpropyl)amino]-1H-benzimidazole-4-carboxamide, (190) N-(3-chloro-2-methyl phenyl)-6-{[(2,5-dichlorophenyl)carbonyl]amino}-2-[(2-hydroxy-2-methylpropyl)amino]-1H-benzimidazole-4-carboxamide, (191) N-(3-chloro-2-methylphenyl)-6-{[(2,5-dichlorophenyl)carbonyl]amino}-2 [(2-methoxy-2-methylpropyl)amino]-1H-benzimidazole-4-carboxamide, (192) N-(3-chloro-2-methylphenyl)-6-{[(2,5-dichlorophenyl)carbonyl]amino}-2-{[2-(propan-2-yloxy)ethyl]amino}-1H-benzimidazole-4-carboxamide, (193) 6-{[(2-chloro-6-fluorophenyl)carbonyl]amino}-N-(3-chloro-2-methylphenyl)-2-{[2-(propan-2-yloxy)ethyl]amino}-1H-benzimidazole-4-carboxamide, (194) 2-[(2-tert-butoxyethyl)amino]-6-{[(2-chloro-6-fluorophenyl)carbonyl]amino}-N-(3-chloro-2-methylphenyl)-1H-benzimidazole-4-carboxamide, (195) 6-{[(2-chloro-6-fluorophenyl)carbonyl]amino}-N-(3-chloro-2-methylphenyl)-2-[(3-methoxy-2,2-dimethylpropyl)amino]-1H-benzimidazole-4-carboxamide, (196) 6-{[(2-chloro-6-fluorophenyl)carbonyl]amino}-N-(3-chloro-2-methylphenyl)-2-[(2-methoxy-2-methylpropyl)amino]-1H-benzimidazole-4-carboxamide, (197) 6-{[(2-chloro-6-fluorophenyl)carbonyl]amino}-N-(3-chloro-2-methylphenyl)-2-{[(2S)-tetrahydrofuran-2-ylmethyl]amino}-1H-benzimidazole-4-carboxamide, (198) 6-{[(2-chloro-6-fluorophenyl)carbonyl]amino}-N-(3-chloro-2-methylphenyl)-2-{[(2R)-tetrahydrofuran-2-ylmethyl]amino}-1H-benzimidazole-4-carboxamide, (199) 6-{[(2-chloro-6-fluorophenyl)carbonyl]amino}-N-(3-chloro-2-methylphenyl)-2-[(3-hydroxy-2,2-dimethylpropyl)amino]-1H-benzimidazole-4-carboxamide, (200) 6-{[(2-chloro-6-fluorophenyl)carbonyl]amino}-N-(3-chloro-2-methylphenyl)-2-{[(2S)-1-hydroxy-3-methylbutan-2-yl]amino}-1H-benzimidazole-4-carboxamide, (201) N-(3-chloro-4-methylphenyl)-2-(dimethylamino)-6-({[2-(trifluoromethyl)phenyl]carbonyl}amino)-1H-benzimidazole-4-carboxamide, (202) N-(4-tert-butylphenyl)-2-(dimethylamino)-6-({[2 (trifluoromethyl)phenyl]carbonyl}amino)-1H-benzimidazole-4-carboxamide, (203) N-(2,3-dihydro-1H-inden-5-yl)-2-(dimethylamino)-6-({[2-(trifluoromethyl)phenyl]carbonyl}amino)-1H-benzimidazole-4-carboxamide, (204) 6-{[(2-chloro-6-fluorophenyl)carbonyl]amino}-N-(3-chloro-4-methylphenyl)-2-(di methyl amino)-1H-benzimidazole-4-carboxamide, (205) N-(3-chloro-4-methylphenyl)-6-{[(2,6-dichlorophenyl)carbonyl]amino}-2-(dimethylamino)-1H-benzimidazole-4-carboxamide.

(206) N-(3-chloro-4-methylphenyl)-6-{[(2,5-dichlorophenyl)carbonyl]amino}-2-(dimethylamino)-1H-benzimidazole-4-carboxamide, (207) N-(3-chloro-2-methylphenyl)-2-cyclopropyl-6-{[(2,5 dichlorophenyl)carbonyl]amino}-1H-benzimidazole-4-carboxamide, (208) N-(3-chloro-4-methylphenyl)-2-cyclopropyl-6-{[(2,5-dichlorophenyl)carbonyl]amino}-1H-benzimidazole-4-carboxamide, (209) N-(3-chloro-2-methylphenyl)-6-{[(2,5-dichlorophenyl)carbonyl]amino}-2-(1-methylcyclopropyl)-1H-benzimidazole-4-carboxamide, (210) N-(3-chloro-4-methylphenyl)-6-{[(2,5-dichlorophenyl)carbonyl]amino}-2-(1-methylcyclopropyl)-1H-benzimidazole-4-carboxamide, (211) N-(3-chloro-2-methylphenyl)-2-(methoxymethyl)-6-({[2-(methylsulfonyl)phenyl]carbonyl}amino)-1H-benzimidazole-4-carboxamide, (212) N-(3-chloro-4-methylphenyl)-6-{[(2,5-dichlorophenyl)carbonyl]amino}-2-(2-methoxy ethyl)-1H-benzimidazole-4-carboxamide, (213) 2-(methoxymethyl)-N-phenyl-6-({[2-(trifluoromethyl)phenyl]carbonyl}amino)-1H-benzimidazole-4-carboxamide, (214) 2-(methoxymethyl)-N-propyl-6-({[2-(trifluoromethyl)phenyl]carbonyl}amino)-1H-benzimidazole-4-carboxamide, (215) 2-(methoxymethyl)-N-(pyridin-3-yl)-6-({[2-(trifluoromethyl)phenyl]carbonyl}amino)-1H-benzimidazole-4-carboxamide, (216) N-benzyl-2-(methoxymethyl)-6-({[2-(trifluoromethyl)phenyl]carbonyl}amino)-1H-benzimidazole-4-carboxamide, (217) N-(cyclohexylmethyl)-2-(methoxymethyl)-6-({[2-(trifluoromethyl)phenyl]carbonyl}amino)-1H-benzimidazole-4-carboxamide, (218) 2-(methoxymethyl)-N-(naphthalen-1-yl)-6-({[2-(trifluoromethyl)phenyl]carbonyl}amino)-1H-benzimidazole-4-carboxamide, (219) 2-(methoxymethyl)-N-(thiophen-3-yl)-6-({[2-(trifluoromethyl)phenyl]carbonyl}amino)-1H-benzimidazole-4-carboxamide, (220) N-(2,1,3-benzothiadiazol-4-yl)-2-(methoxymethyl)-6-({[2-(trifluoromethyl)phenyl]carbonyl}amino)-1H-benzimidazole-4-carboxamide, (221) N-(1,1-di oxido-1-benzothiophen-6-yl)-2-(methoxymethyl)-6-({[2 (trifluoromethyl)phenyl]carbonyl}amino)-1H-benzimidazole-4-carboxamide, (222) 2-(methoxymethyl)-N-(thiophen-2-ylmethyl)-6-({[2-(trifluoromethyl)phenyl]carbonyl}amino)-1H-benzimidazole-4-carboxamide, (223) N-(1H-indol-5-yl)-2-(methoxymethyl)-6-({[2-(trifluoromethyl)phenyl]carbonyl}amino)-1H-benzimidazole-4-carboxamide, (224) N-(1,3-benzothiazol-211)-2-(methoxymethyl)-6-({[2-(trifluoromethyl)phenyl]carbonyl}amino)-1H-benzimidazole-4-carboxamide, (225) N-(2,2-dimethylpropyl)-2-(methoxymethyl)-6-({[2-(trifluoromethyl)phenyl]carbonyl}amino)-1H-benzimidazole-4-carboxamide, (226) 2-(methoxymethyl)-N-(thiophen-2-yl)-6-({[2 (trifluoromethyl)phenyl]carbonyl}amino)-1H-benzimidazole-4-carboxamide, (227) N-(5-chloro-1,3-benzoxazol-2-yl)-2-(methoxymethyl)-6-({[2-(trifluoromethyl)phenyl]carbonyl}amino)-1H-benzimidazole-4-carboxamide, (228) N-(2-benzylphenyl)-2-(methoxymethyl)-6-({[2-(trifluoromethyl)phenyl]carbonyl}amino)-1H-benzimidazole-4-carboxamide, (229) 2-(methoxymethyl)-N-(quinolin-8-yl)-6-({[2-(trifluoromethyl)phenyl]carbonyl}amino)-1H-benzimidazole-4-carboxamide, (230) N-(cycloheptylmethyl)-2-(methoxymethyl)-6-({[2-(trifluoromethyl)phenyl]carbonyl}amino)-1H-benzimidazole-4-carboxamide, (231) N-(1,3-benzoxazol-2-yl)-2-(methoxymethyl)-6-({[2-(trifluoromethyl)phenyl]carbonyl}amino)-1H-benzimidazole-4-carboxamide, (232) N-(6-chloro-1,3-benzoxazol-2-yl)-2-(methoxymethyl)-6-({[2-(trifluoromethyl)phenyl]carbonyl}amino)-1H-benzimidazole-4-carboxamide, (233) N-[3-chloro-2-(hydroxymethyl)phenyl]-2-(methoxymethyl)-6-({[2-(trifluoromethyl)phenyl]carbonyl}amino)-1H-benzimidazole-4-carboxamide, (234) N-(3-chloro-2-methylphenyl)-6-{[(3-fluoropyridin-2-yl)carbonyl]amino}-2-(methoxymethyl)-1H-benzimidazole-4-carboxamide, (235) N-(3-chloro-2-methylphenyl)-6-{[(3-chloropyridin-4-yl)carbonyl]amino}-2-(methoxymethyl)-1H-benzimidazole-4-carboxamide, (236) N-(3-chloro-2-methylphenyl)-6-{[(3,5-dichloropyridin-4-yl)carbonyl]amino}-2-(methoxymethyl)-1H-benzimidazole-4-carboxamide, (237) 6-{[(5-butoxy-2-chlorophenyl)carbonyl]amino}-N-(3-chloro-2-methylphenyl)-2-(methoxymethyl)-1H-benzimidazole-4-carboxamide, (238) 6-({[2-chloro-5-(2,2-difluoroethoxy)phenyl]carbonyl}amino)-N-(3-chloro-2-methylphenyl)-2-(methoxymethyl)-1H-benzimidazole-4-carboxamide, and (239) N-(3-chloro-2-methylphenyl)-6-({[2-chloro-5-(4,4,4-trifluorobutoxy)phenyl]carbonyl}amino)-2-(methoxymethyl)-1H-benzimidazole-4-carboxamide, or a tautomer of the compound, or a pharmaceutically acceptable salt thereof.

(9) The prophylactic and/or therapeutic agent for chronic prostatitis/chronic pelvic pain syndrome according to the above-described items (2) to (8), wherein the mPGES-1 inhibitor is a compound selected from the group consisting of:

N-(3-chloro-2-methylphenyl)-2-(methoxymethyl)-6-({[2-(trifluoromethyl)phenyl]carbonyl}amino)-1H-benzimidazole-4-carboxamide, N-(3-chloro-2-methylphenyl)-2-(methoxymethyl)-6-({[2-(trifluoromethyl)phenyl]carbonyl}amino)-1H-benzimidazole-4-carboxamide hydrochloride, N-(3-chloro-2-methylphenyl)-2-(methoxymethyl)-6-({[2-(trifluoromethyl)phenyl]carbonyl}amino)-1H-benzimidazole-4-carboxamide methanesulfonate, N-(3-chloro-2-methylphenyl)-2-(methoxymethyl)-6-({[2-(trifluoromethyl)phenyl]carbonyl}amino)-1H-benzimidazole-4-carboxamide 4-methylbenzenesulfonate, N-(3-chloro-2-methylphenyl)-2-(methoxymethyl)-6-({[2-(trifluoromethyl)phenyl]carbonyl}amino)-1H-benzimidazole-4-carboxamide sulfate, N-(3-chloro-2-methylphenyl)-2-(1-methylcyclopropyl)-6-({[2-(trifluoromethyl)phenyl]carbonyl}amino)-1H-benzimidazole-4-carboxamide, N-(3-chloro-2-methylphenyl)-2-(1-methylcyclopropyl)-6-({[2-(trifluoromethyl)phenyl]carbonyl}amino)-1H-benzimidazole-4-carboxamide hydrochloride, N-(3-chloro-2-methylphenyl)-2-(1-methylcyclopropyl)-6-({[2-(trifluoromethyl)phenyl]carbonyl}amino)-1H-benzimidazole-4-carboxamide methanesulfonate, N-(3-chloro-2-methylphenyl)-2-(1-methylcyclopropyl)-6-({[2-(trifluoromethyl)phenyl]carbonyl}amino)-1H-benzimidazole-4-carboxamide 4-methylbenzenesulfonate, N-(3-chloro-2-methylphenyl)-2-(1-methylcyclopropyl)-6-({[2 (trifluoromethyl)phenyl]carbonyl}amino)-1H-benzimidazole-4-carboxamide sulfate, N-(3-chloro-4-methylphenyl)-6-{[(2,5-dichlorophenyl)carbonyl]amino}-2-(dimethylamino)-1H-benzimidazole-4-carboxamide, N-(3-chloro-4-methylphenyl)-6-{[(2,5-di chlorophenyl)carbonyl]amino}-2-(dimethylamino)-1H-benzimidazole-4-carboxamide hydrochloride, N-(3-chloro-4-methylphenyl)-6-{[(2,5-dichlorophenyl)carbonyl]amino}-2-(dimethylamino)-1H-benzimidazole-4-carboxamide methanesulfonate, N-(3-chloro-4-methylphenyl)-6-{[(2,5-dichlorophenyl)carbonyl]amino}-2-(dimethylamino)-1H-benzimidazole-4-carboxamide 4-methylbenzenesulfonate, and N-(3-chloro-4-methylphenyl)-6-{[(2,5-dichlorophenyl)carbonyl]amino}-2-(dimethylamino)-1H-benzimidazole-4-carboxamide sulfate, or a tautomer of the compound, or a pharmaceutically acceptable salt thereof.

(10) A pharmaceutical composition for prevention and/or treatment of chronic prostatitis/chronic pelvic pain syndrome, the pharmaceutical composition containing an mPGES-1 inhibitor and a pharmaceutically acceptable carrier thereof.

(11) An mPGES-1 inhibitor for use in prevention and/or treatment of chronic prostatitis/chronic pelvic pain syndrome.

(12) Use of an mPGES-1 inhibitor for the manufacture of a medicine for prevention and/or treatment of chronic prostatitis/chronic pelvic pain syndrome.

(13) A method for preventing and/or treating chronic prostatitis/chronic pelvic pain syndrome, the method comprising administering an mPGES-1 inhibitor to a subject in need of the mPGES-1 inhibitor.

Each of the element described above can be arbitrarily selected and combined.

Advantageous Effects of Invention

The treatment and/or therapeutic agent of the present invention exhibits a therapeutic and/or prophylactic effect for chronic prostatitis/chronic pelvic pain syndrome and is therefore useful for the treatment and/or prevention of chronic prostatitis/chronic pelvic pain syndrome.

BRIEF DESCRIPTION OF DRAWINGS

FIGURE shows the results of performing an evaluation of the analgesic effect of test compounds 1 to 5 in an autoimmune chronic prostatitis model.

DESCRIPTION OF EMBODIMENTS

Embodiments of the invention is described below.

According to an aspect of the invention, there is provided a prophylactic and/or therapeutic agent for chronic prostatitis/chronic pelvic pain syndrome, the agent containing an mPGES-1 inhibitor as an active ingredient.

According to an aspect of the invention, regarding the mPGES-1 inhibitor, a commercially available compound and/or a compound that can be produced by a conventional method in the field of synthetic organic chemistry can be used.

According to an aspect of the invention, the mPGES-1 inhibitor can be used as it is as a medicine but can also be used in the form of a pharmaceutically acceptable salt thereof through a known method. Examples of such a salt include salts of mineral acids such as hydrochloric acid, hydrobromic acid, sulfuric acid, and phosphoric acid: and salts of organic acids such as acetic acid, citric acid, tartaric acid, maleic acid, succinic acid, fumaric acid, p-toluenesulfonic acid, benzenesulfonic acid, and methanesulfonic acid.

For example, hydrochloride of an mPGES-1 inhibitor can be obtained by dissolving the mPGES-1 inhibitor in an alcohol solution, an ethyl acetate solution, or a diethyl ether solution of hydrogen chloride.

According to an aspect of the invention, the mPGES-1 inhibitor may have asymmetric carbon, and each of optical isomers and mixtures thereof can all be used as the prophylactic and/or therapeutic agent of the invention. An optical isomer can be produced by, for example, optically resolving a racemate obtained in the same manner as in the Examples that is described below, by utilizing the basicity of the racemate and by using an optically active acid (tartaric acid, dibenzoyltartaric acid, mandelic acid, 10-camphor-sulfonic acid, or the like), or can be produced by using an optically active compound that has been prepared in advance as a raw material. In addition to that, an optical isomer can also be produced by optical resolution using a chiral column or by asymmetric synthesis.

Furthermore, among mPGES-1 inhibitors, for those capable of forming tautomers, each of tautomers and mixtures thereof can all be used as the prophylactic and/or therapeutic agent of the invention.

According to an aspect of the invention, the mPGES-1 inhibitor is, for example, the above-described compound of Formula [I] (present compound) or a pharmaceutically acceptable salt thereof. The present compound can be produced from a known compound and/or an intermediate that can be easily synthesized, according to the method described in WO 2013/024898 and/or a known method.

With regard to the compound of Formula [I] (present compound), examples of each substituent are as follows.

Examples of the "halogen" include fluorine, chlorine, bromine, and iodine.

Examples of the "alkyl" include linear or branched alkyl having 1 to 8 carbon atoms, and specific examples thereof include methyl, ethyl, n-propyl, isopropyl, n-butyl, isobutyl, sec-butyl, tert-butyl, n-pentyl, isopentyl, n-hexyl, isohexyl, n-heptyl, isoheptyl, and n-octyl. Among them, alkyl having 1 to 6 carbon atoms is preferred, and alkyl having 1 to 3 carbon atoms is more preferred.

Examples of the alkyl moiety of "monoalkylamino", "dialkylamino", "monoalkylaminocarbonyl", "dialkylaminocarbonyl", "alkylcarbonyloxy", "alkyloxycarbonyl", "alkylcarbonyl", "alkylthio", "alkylsulfonyl", "alkylsulfinyl", "alkoxyalkyl", and "alkoxyalkylamino" include those similar to the above-described "alkyl".

Examples of the alkoxy moiety of "alkoxy" include linear or branched alkoxy having 1 to 8 carbon atoms, and specific examples thereof include methoxy, ethoxy, n-propoxy, isopropoxy, n-butoxy, isobutoxy, sec-butoxy, t-butoxy, n-pentyloxy, n-hexyloxy, n-heptyloxy, and n-octyloxy.

Examples of the alkoxy moiety of "alkoxyalkoxy", "alkoxyalkyl", and "alkoxyalkylamino" include those similar to the above-described "alkoxy".

The "heteroaryl" may be a monocyclic or bicyclic aromatic ring having one to three heteroatoms selected from the group consisting of a nitrogen atom, an oxygen atom, and a sulfur atom as constituent atoms. Specific examples thereof include furyl (for example, 2-furyl or 3-furyl), thienyl (for example, 2-thienyl or 3-thienyl), pyrrolyl (for example, 1-pyrrolyl, 2-pyrrolyl, or 3-pyrrolyl), imidazolyl (for example, 1-imidazolyl, 2-imidazolyl, or 4-imidazolyl), pyrazolyl (for example, 1-pyrazolyl, 3-pyrazolyl, or 4-pyrazolyl), triazolyl (for example, 1,2,4-triazol-1-yl, 1,2,4-triazol-3-yl, or 1,2,4-triazol-4-yl), tetrazolyl (for example, 1-tetrazolyl, 2-tetrazolyl, or 5-tetrazolyl), oxazolyl (for example, 2-oxazolyl, 4-oxazolyl, or 5 oxazolyl), isoxazolyl (for example, 3-isoxazolyl, 4-isoxazolyl, or 5-isoxazolyl), oxadiazolyl (for example, 1,3,4-oxadiazol-2-yl), thiazolyl (for example, 2-thiazolyl, 4-thiazolyl, or 5-thiazolyl), thiadiazolyl (for example, 1,3,4-thiadiazolyl, 1,2,4-thiadiazolyl, or 1,2,3-thiadiazolyl), isothiazolyl (for example, 3-isothiazolyl, 4-isothiazolyl, or 5-isothiazolyl), pyridyl (for example, 2-pyridyl, 3-pyridyl, or o4-pyridyl), pyridazinyl (for example, 3 pyridazinyl or 4-pyridazinyl), pyrimidinyl (for example, 2-pyrimidinyl, 4-pyrimidinyl, or 5-pyrimidinyl), pyrazinyl (for example, 2-pyrazinyl), benzothiadiazolyl (for example, 1,2,3-benzothiadiazol-4-yl, 1,2,3-benzothiadiazol-5-yl, 2,1,3-benzothiadiazol-4-yl, or 2,1,3-benzothiadiazol-5-yl), benzothiazolyl (for example, benzothiazol-2-yl, benzothiazol-4-yl, benzothiazol-5-yl, benzothiazol-6-yl, or benzothiazol-7-yl), indolyl (for example, indol-3-yl, indol-4-yl, indol-5-yl, indol-6-yl, or indol-7-yl), benzothiophenyl (for example, 1-benzothiophen-2-yl, 1-benzothiophen-3-yl, 1-benzothiophen-4-yl, 1-benzothiophen-5-yl, 1-benzothiophen-6-yl, or 1-benzothiophen-7-yl), 1,1-dioxo-1-benzothiophenyl (for example, 1,1-dioxo-1-benzothiophen-2-yl, 1,1-dioxo-1-benzothiophen-3-yl, 1,1-dioxo-1-benzothiophen-4-yl, 1,1-dioxo-1-benzothiophen-5-yl, 1,1-dioxo-1-benzothiophen-6-yl, or 1,1 dioxo-1-benzothiophen-7-yl), quinolyl(quinolin-2-yl, quinolin-3-yl, quinolin-4-yl, quinolin-5-yl, quinolin-6-yl, quinolin-7-yl, or quinolin-8-yl), and 1,3-benzoxazol-2-yl.

Examples of the heteroaryl moiety of "heteroarylmethyl" include those similar to the above-described "heteroaryl".

Examples of the "saturated cyclic amino" include a 4-membered to 7-membered saturated cyclic amino group having one or two N atoms, the cyclic amino group optionally having one O or S as a ring-constituting atom and optionally being substituted with oxo, and specific examples thereof include 1-azetidinyl, 1-pyrrolidinyl, 1-imiazolidinyl, piperidino, 1-piperazinyl, 1-tetrahydropyrimidinyl, 4-morpholino, 4-thiomorpholino, 1-homopiperazinyl, and 2-oxo-oxazolidin-3-yl.

Examples of the saturated cyclic amino moiety of "saturated cyclic aminocarbonyl" include those similar to the above-described "saturated cyclic amino".

Examples of the "saturated heterocyclic group" include a 4-membered to 6-membered saturated heterocyclic group having one N or O as a ring-constituting atom, and specific examples thereof include 2-pyrrolidinyl, 3-pyrrolidinyl, 2-piperidinyl, 3-piperidinyl, 4-piperidinyl, 2-oxetanyl, 3-oxetanyl, 2-tetrahydrofuranyl, and 3-tetrahydrofuranyl.

Examples of the "cycloalkyl" include cycloalkyl having 3 to 8 carbon atoms, and specific examples thereof include cyclopropyl, cyclobutyl, cyclopentyl, cyclohexyl, cycloheptyl, and cyclooctyl.

Examples of the cycloalkyl moiety of "cycloalkylmethyl" include those similar to the above-described "cycloalkyl".

Examples of "naphthyl" include 1-naphthyl and 2-naphthyl.

Examples of "pyridyl" include 2-pyridyl, 3-pyridyl, and 4-pyridyl.

Examples of "alkynyl" include linear or branched alkynyl having 2 to 6 carbon atoms. Specific examples include ethynyl, 1-propynyl, 1-butynyl, 1-pentynyl, 2-propynyl, 2-butynyl, 3-butynyl, 1-methyl-2-propynyl, 2-pentynyl, 3-pentynyl, and 4-pentynyl.

According to an aspect of the invention, the mPGES-1 inhibitor is, for example, each of the above-described compounds (1) to (239) or a tautomer of the compound, or a pharmaceutically acceptable salt thereof, and the mPGES-1 inhibitor is preferably N-(3-chloro-2-methylphenyl)-2-(methoxymethyl)-6-({[2-(trifluoromethyl)phenyl]carbonyl}amino)-1H-benzimidazole-4-carboxamide, N-(3-chloro-2-methylphenyl)-2-(1-methylcyclopropyl)-6-({[2-(trifluoromethyl)phenyl]carbonyl}amino)-1H-benzimidazole-4-carboxamide, or N-(3-chloro-4-methylphenyl)-6-{[(2,5-dichlorophenyl)carbonyl]amino}-2-(dimethylamino)-1H-benzimidazole-4-carboxamide, or a pharmaceutically acceptable salt thereof, and more preferably N-(3-chloro-2-methylphenyl)-2-(methoxymethyl)-6-({[2-(trifluoromethyl)phenyl]carbonyl}amino)-1H-benzimidazole-4-carboxamide, N-(3-chloro-2-methylphenyl)-2-(methoxymethyl)-6-({[2-(trifluoromethyl)phenyl]carbonyl}amino)-1H-benzimidazole-4-carboxamide hydrochloride, N-(3-chloro-2-methylphenyl)-2-(methoxymethyl)-6-({[2-(trifluoromethyl)phenyl]carbonyl}amino)-1H-benzimidazole-4-carboxamide 4-methylbenzenesulfonate, N-(3-chloro-2-methylphenyl)-2-(1-methylcyclopropyl)-6-({[2-(trifluoromethyl)phenyl]carbonyl}amino)-1H-benzimidazole-4-carboxamide hydrochloride, or N-(3-chloro-4-methylphenyl)-6-{[(2,5-di chlorophenyl)carbonyl]amino}-2-(dimethylamino)-1H-benzimidazole-4-carboxamide hydrochloride.

When the present compound or a pharmaceutically acceptable salt thereof is administered as a medicine, the present compound or a pharmaceutically acceptable salt thereof is administered as a pharmaceutical composition containing the present compound or a pharmaceutically acceptable salt thereof as it is or in a pharmaceutically acceptable non toxic and inert carrier, for example, at a proportion of 0.001% to 99.5%, and preferably 0.1% to 90%, to a mammal including a human.

As the carrier, one or more kinds of diluents, fillers, and other auxiliary agents for formulation, which are solid, semi-solid, or liquid, are used. It is desirable that the pharmaceutical composition according to the invention is administered in a unit dosage form. The pharmaceutical composition can be administered by interstitial administration, peroral administration, intravenous administration, topical administration (percutaneous administration, ocular instillation, intraperitoneal, intraperitoneal, intrapleural, and the like), or transrectally. Further, the pharmaceutical composition is to be administered in a dosage form appropriate for these administration methods.

It is desirable to adjust the dosage as a medicine after taking the conditions of the patient, such as age, body weight, the type and severity of the disease, the route of administration, the type of the compound of the invention, whether it is a salt or not, the type of the salt, and the like into consideration; however, usually, as the amount as an active ingredient of the compound of the invention or a pharmaceutically acceptable salt thereof for an adult, in the case of oral administration, the dosage is appropriately in the range of 0.01 mg to 5 g/adult, and preferably in the range of 1 mg to 500 mg/adult, per day. In some cases, a dosage equal to or less than this may be sufficient, or in contrast, a dosage greater than this may be needed. Usually, the compound or a pharmaceutically acceptable salt thereof can be administered once or in several divided doses a day, or in the case of intravenous administration, the compound or a pharmaceutically acceptable salt thereof can be rapidly administered or can be administered continuously within 24 hours.

EXAMPLES

Hereinafter, the present invention is described in more detail by way of Reference Examples, Examples, Test Examples, and Preparation Examples; however, the invention is not be limited to these only.

The test compounds used in Test Examples 1 and 2 are as follows.

According to the description of Examples 1 to 249 of WO 2013/024898, the compounds used in Test Examples 1 and 2 were prepared and used. The activity data of the compounds used in Test Examples 1 and 2 are as described in Tables 1 to 17 of WO 2013/024898.

Test Example 1 Test for mPGES-1 Inhibitory Activity

A mPGES-1 microsome was prepared from CHO-K1 cells transiently transfected with a plasmid encoding human mPGES-1 cDNA. The mPGES-1 microsome was diluted in a potassium phosphate buffer solution pH 7.4 containing reduced glutathione, a DMSO solution of a test compound or DMSO alone (DMSO final concentration of 1% in both cases) was added thereto, and the mixture was incubated at 4° C. for 20 minutes. Next, a solution prepared by dissolving PGH2 substrate to a final concentration of 1 μM was added to the mixture to initiate an enzymatic reaction, and the mixture was incubated at 4° C. for 60 seconds. A solution of ferric chloride and a citrate (final concentrations of 1 mg/mL and 50 mM, respectively) was added to the mixture to complete the reaction. PGE2 thus formed was quantified by using an HTRF kit (Cisbio International product catalogue #62P2APEC). A solution free of the test compound was used as a positive control, and a solution free of the test compound and the microsome was used as a negative control. 100% activity was defined as PGE2 production in the positive control minus PGE2 production in the negative control. Next, the IC50 value was calculated by using a standard method.

Test Example 2 Test for Inhibition of PGE2 and PGF2α Production in A549 Cells Human A549 cells were seeded at a rate of $2\times10^4$ cells in 100 μL/well (96-well plate), and the cells were incubated overnight. After the medium was removed, the cells were washed with a phosphate buffered saline, and then the culture medium was replaced with 3% FBS-containing RPMI medium containing a DMSO solution of a test compound or DMSO alone (DMSO final concentration of 0.1% in both cases). The cells were incubated for 60 minutes, subsequently IL-1β (5 ng/well) was added thereto, and the cells were incubated at 37° C. for 24 hours. Subsequently, PGE2 in the medium was measured by using an HTRF kit (Cisbio International product catalogue #62P2APEC), and PGF2α was measured by using an EIA kit (Cayman Chemical Company product catalogue #516011). A solution free of the test compound was used as a positive control, and a solution free of the test compound and IL-1β was used as a negative control. 100% activity was defined as PGE2 and PGF2α production in the positive control minus PGE2 and PGF2α production in the negative control. Next, the IC50 value was measured by using a standard method.

The test compounds used in Test Examples 3 to 8 are as follows.

Test Compound 1 and Test Compound 2:

According to the description of Example 239 and Example 89 of WO 2013/024898, the compounds of test compound 1: N-(3-chloro-2-methylphenyl)-2-(methoxymethyl)-6-({[2-(trifluoromethyl)phenyl]carbonyl}amino)-1H-benzimidazole-4-carboxamide 4-methylbenzenesulfonate, and test compound 2: N-(3-chloro-2-methylphenyl)-2-[1-(trifluoromethyl)cyclopropyl]-6-({[2-(trifluoromethyl)phenyl]carbonyl}amino)-1H-benzimidazole-4-carboxamide were prepared and used (hereinafter, also referred to as test compound 1 and test compound 2).

Test Compound 3:

According to the description of Example 9 of WO 2011/023812, test compound 3: N-cyclopentyl-1-(1-isopropyl-5,6-dimethyl-1H-benzo[d]imidazol-2-yl)piperidine-4-carboxamide was prepared and used.

Test Compound 4:

According to the description of Example 2 of WO 2017/073709, test compound 4: N-[4-chloro-3-(5-cyano-6-oxo-4-thiophen-3-yl-1,6-dihydropyrimidin-2-yl)benzyl]-2,2-dimethylpropionamide was prepared and used.

Regarding CANEPHRON (registered trademark) N, a commercially available product was purchased and used.

Test Example 3: Evaluation of Analgesic Effect in Autoimmune Chronic Prostatitis Model The analgesic effect of the test compounds 1 to 4 was evaluated by the following method by using an autoimmune chronic prostatitis (experimental autoimmune prostatitis: EAP) model generally used as a chronic prostatitis model.

1. Method for preparing prostate-specific antigen (Prostate Antigen; PAg)

Prostate was extracted from a 14-week old male Wistar rat (manufactured by Japan SLC, Inc.), and the prostate was homogenized in a PBS (Cat. No. 045-29795, manufactured by FUJIFILM Wako Pure Chemical Corporation) prepared by adding cOmplete (registered trademark) Mini, EDTA-free (Cat. No. 11836170001, manufactured by Roche Diagnostics GmbH) and ice-cooling, by using a handy microhomogenizer (NS-310E, manufactured by Microtec Co., Ltd.), and then the resultant was centrifuged at 10000×g at 4° C. for 30 minutes by using a centrifuge (Allegra X-30R, manufactured by Beckman Coulter, Inc.) to collect a supernatant. The protein concentration was measured by using a DC (trademark) protein assay kit (Cat. No. 500-0112, manufactured by BIO-RAD Laboratories, Inc.) and a microplate reader SpectraMax (registered trademark) M5 (manufactured by Molecular Devices, LLC.), and then the supernatant was stored at −20° C.

2. Method for Preparing EAP Model

PAg and Complete Freund's adjuvant (Cat. No. 263810, manufactured by Becton, Dickinson and Company) were mixed in equal amounts to produce an emulsion having a PAg protein concentration of 5 mg/250 μL. Under isoflurane anesthesia, initial immunization was performed by subcutaneously administering 250 μL of the produced emulsion per rat to the foot soles and ridge parts of both hind limbs of 9-week old male Wistar rats (manufactured by Japan SLC, Inc.). After 28 days from the initial immunization, the same treatment was performed as booster immunization. In a sham-treatment group, an emulsion obtained by mixing physiological saline (Cat. No. 35081517, manufactured by Otsuka Pharmaceutical Factory. Inc.) and Complete Freund's adjuvant in equal amounts was administered (see Prostate, 2018 November; 78(15): 1157-1165).

3. Grouping Method

After 37 days from the initial immunization, the pre value was measured by using the following method for pain evaluation, and grouping was performed such that there was no significant difference in both the pain response rate and the AUC at each stimulus intensity. Grouping was performed by stratified random assignment by using SAS version 9.3 and EXSUS version 8.1.

4. Method for Pain Evaluation

After 42 days from the initial immunization, a substance to be tested was prepared by using a 0.5% aqueous solution of methyl cellulose as a medium to a concentration of 100 mg/kg in terms of a free substance, the substance to be tested was orally administered at a rate of 10 mL/kg, and pain evaluation was carried out 4 hours after the administration. Rats were placed on a wire mesh for 30 minutes prior to the evaluation and were acclimatized. Three kinds of 0.4 g, 1 g, or 4 g von Frey filaments (Touch Test (registered trademark), Cat. No. NC12775-06, NC12775-08, NC12775-11, manufactured by North Coast Medical, Inc.) having different stimulus intensities were pressed for 1 to 2 seconds against the lower abdomen parts of the rats from under the wire mesh, and thereby the presence or absence of escape response (escaping, licking the stimulation site, and the like) was observed. Stimulation was performed five times each at each stimulus intensity in order from a filament with the weakest stimulus intensity, the proportion showing the escape response was calculated as the escape response ratio (%), and the area under curve (AUC) was calculated from a line graph created from the stimulus intensity and the escape response ratio.

5. Statistical Analysis

Calculation of the summary statistics and statistical analysis were performed using Microsoft Office Excel 2016 (registered trademark), SAS version 9.3, and EXSUS version 8.1. The mean value and standard error of the AUC of each group were determined, and Student's t-test was performed between the Sham group and an EAP model-medium administered group, and between the EAP model-medium administered group and an EAP model drug administered group.

6. Test Results

The analgesic effect of the test compounds 1 to 5 in the EAP model is shown in FIGURE.

Test Example 4: Evaluation of Anti-Inflammatory Effect in Normal Human Prostate Stromal Cells 1. Cell Culture Normal human prostate stromal cells (WPMY 1 cells, Cat. No. CRL-2854 (trademark)) purchased from ATCC (registered trademark) were subcultured using a growth medium under the conditions of 37° C. and 5% $CO_2$. As the growth medium, DMEM (Cat. No. 08458-45, manufactured by NACALAI TESQUE, INC.) containing inactivated fetal bovine serum (Cat. No. SH30910, manufactured by GE Healthcare) at a final concentration of 5%, as well as penicillin at a final concentration of 20 U/mL and streptomycin at a final concentration of 20 μg/mL (penicillin-streptomycin mixed solution, Cat. No. 26253-84, manufactured by NACALAI TESQUE, INC.) was used.

2. Cell Seeding and Drug Treatment

The day before the treatment with each compound to be tested, WPMY 1 cells were suspended in a growth medium, and the cells were seeded at 57,000 cells/well on a Falcon (registered trademark) Cell Culture 12-well Multi-well Plate (Cat. No. 353043, manufactured by Corning, Incorporated). The WPMY 1 cells seeded on the 12-well plate were cultured overnight under the conditions of 37° C. and 5% $CO_2$.

The day after seeding, each substance to be tested was treated. First, a 10 mM DMSO solution of drug was prepared using DMSO (Cat. No. 13445-74, manufactured by NACALAI TESQUE, INC.), and the solution was diluted to 10 μM using an assay medium. A 1000 mg/mL DMSO solution of CANEPHRON was prepared and diluted to 1000 μg/mL using an assay medium. As the assay medium, DMEM (Cat. No. 08458-45, manufactured by NACALAI TESQUE, INC.) containing inactivated fetal bovine serum (Cat. No. SH30910, manufactured by GE Healthcare) at a final concentration of 2%, as well as penicillin at a final concentration of 20 U/mL and streptomycin at a final concentration of 20 μg/mL (penicillin-streptomycin mixed solution, Cat. No. 26253-84, manufactured by NACALAI TESQUE, INC.) was used. The growth medium was removed, the medium was replaced with an assay medium containing each substance to be tested, and then the cells were cultured for 24 hours under the conditions of 37° C. and 5% $CO_2$.

3. Cytokine Stimulation

Cytokine stimulation was performed 24 hours after the treatment with each substance to be tested. An assay medium containing 1 ng/mL each of IL-17 (Cat. No. 200-17, manufactured by PeproTech, Inc.), TNF-α (Cat. No. 300-01A, manufactured by PeproTech, Inc.), and IFN-γ (Cat. No. 300-02, manufactured by PeproTech, Inc.) was prepared and used as a medium for cytokine stimulation. Each substance to be tested was diluted by a method similar to that used the day before by using the medium for cytokine stimulation, and cells were treated with each substance to be treated and cytokine. The cells were cultured for 5 hours under the conditions of 37° C. and 5% $CO_2$, and the cells were collected.

4. Gene Expression Analysis

Total RNA was extracted from cells according to the manufacturer's protocol by using RNeasy (registered trademark) Mini Kit (Cat. No. 74106, manufactured by QIAGEN), and the RNA concentration was measured with NanoDrop (trademark) ONE (Cat. No. ND-ONE-W, manufactured by Thermo Scientific, Inc.). 500 ng of RNA was subjected to reverse transcription using ReverTra Ace (registered trademark) qPCR RT Master Mix (Cat. No. FSQ-201, manufactured by TOYOBO CO., LTD.) and Biometra Tadvanced 96SG (manufactured by BM Equipment Co., Ltd.). The cDNA obtained by reverse transcription, TB Green (registered trademark) Premix Ex Taq II (Cat. No. RR820, manufactured by Takara Bio Inc.), and LightCycler (registered trademark) 480 real-time PCR system (manufactured by Roche Diagnostics GmbH) were used to evaluate the gene expression level of CCL2. Regarding the primers of CCL2, Fw: AGCAGCAAGTGTCCCAAAGA and Rv: GGTGGTCCATGGAATCCTGA were used.

The ratio of the mRNA level of each treated group with respect to the level of an NT (non-treated) group was calculated by using the A threshold cycle (Ct) method (2-ΔΔCt) to calculate the rate of change. All the data were corrected by means of GAPDH. Regarding the PCR conditions, the system was maintained at 95° C. for 10 minutes, and then 45 cycles of maintaining at 95° C. for 15 seconds and at 60° C. for 1 minute were repeated.

5. Test Results

The test compounds suppressed the expression of inflammatory cytokine/chemokine (CCL2) in normal human prostate stromal cells (WPMY-1 cells) and exhibited anti-inflammatory effect (Table 1).

TABLE 1

| Test compound | Level of Expression of CCL2 when the level of expression by vehicle was taken as 1 |
|---|---|
| 1 | 0.6792 |
| 2 | 0.7813 |
| 3 | 1.0119 |
| 4 | 1.2215 |
| CANEPHRON ® N | 0.9571 |

Test Example 5: Evaluation of Anti-Inflammatory Effect in Autoimmune Chronic Prostatitis Model 1. Preparation of Protein Solution An EAP model rat was produced by a method similar to Test Example 1, and a substance to be tested was administered for 42 days from the initial immunization. After 42 days from the initial immunization, the ventral lobe of prostate was collected, placed in a 2-mL tube, frozen with liquid nitrogen, and then stored at −80° C.

A protein solution was prepared by adding T PER (Cat. No. 78510, manufactured by Thermo Scientific, Inc.) containing cOmplete (trademark) Mini, EDTA-free into the 2-mL tube containing prostate in an amount of 1 mL with respect to 100 mg of the prostate tissue weight, homogenizing the prostate by using a handy microhomogenizer (NS-310E, manufactured by Microtec Co., Ltd.), centrifuging the resultant at 14000×g and 4° C. for 30 minutes by using himac (registered trademark) CT15RE (manufactured by Koki Holdings Co., Ltd.), and collecting the supernatant.

2. Measurement of Amount of Cytokines/Chemokines

The amounts of 23 kinds of cytokines/chemokines were measured according to the manufacturer's protocol by using a cytokine assay kit (Rat 23-plea panel) and Bio-Plex system (manufactured by Bio-RAD Laboratories, Inc.). Furthermore, the total protein amount was measured by using a DC (trademark) protein assay kit (Cat. No. 500-0112, manufactured by BIO-RAD Laboratories, Inc.) and a microplate reader SpectraMax (registered trademark) M5 (manufactured by BIO-RAD LaboratoriesMolecular Devices, LLC.), and then the cytokine/chemokine concentration per 1 mg of the total protein amount was calculated.

2. Test Results

The test compounds suppressed the expression of inflammatory cytokines/chemokines (IL-1β, CCL2, CCL3, and CCL5) in the EAP model and exhibited anti-inflammatory effect.

Test Example 6: Evaluation of Analgesic Effect in Hormone-Induced Chronic Prostatitis (Hormone/Castration-Induced Prostatitis; HCP) Model 1. Method for Producing HCP Model Under isoflurane anesthesia, male Wistar retired rats (manufactured by Charles River Laboratories Japan, Inc.) were subjected to castration surgery, and 0.25 mg/kg of 17β estradiol (Cat. No. 14541-61, manufactured by NACALAI TESQUE, INC.) was subcutaneously administered at a rate of 2 mL/kg once a day for 30 days from the day of surgery, by using sesame oil (Cat. No. S3547, manufactured by Sigma-Aldrich). A sham-treatment group was subjected to sham surgery and was similarly administered with sesame oil as the medium (see Prostate, 2019 April; 79(5): 446-453).

2. Drug Treatment

A substance to be tested was administered for 30 days from the day of surgery.

3. Method for Pain Evaluation

Evaluation was carried out by a method similar to that of Test Example 3.

4. Statistical Analysis

Evaluation was carried out by a method similar to that of Test Example 3.

5. Test Results

The test compounds exhibited analgesic effect in the HCP model.

Test Example 7: Evaluation of Analgesic Effect in Formalin-Induced Prostatitis Model 1. Method for Producing Formalin-Induced Prostatitis Model Under isoflurane anesthesia, a median incision was made in the lower abdomen part of a 7-week old male SD rat (manufactured by Japan SLC, Inc.) to expose prostate. 25 μL each of a 5% formalin solution produced by mixing a 10% neutral buffered formalin solution (Cat. No. 062-01661, manufactured by FUJIFILM Wako Pure Chemical Corporation) and physiological saline (Cat. No. 35081517, manufactured by Otsuka Pharmaceutical Factory, Inc.) in equal amounts was injected into the right and left ventral lobes of the prostate, subsequently the lower abdomen part was sutured, and antibiotic substance Cefalexin (Cat. No. 034-11052, manufactured by FUJIFILM Wako Pure Chemical Corporation) was subcutaneously administered at a rate of 15 mg/kg. In a sham-treatment group, 25 μL each of physiological saline was injected into the right and left ventral lobes of the prostate (see Int Neurourol J. 2018 June; 22(2): 90-98).

2. Drug Treatment

A substance to be tested was administered twice a day for 7 days from the day of model production.

3. Method for Pain Evaluation

Evaluation was carried out by a method similar to that of Test Example 1, 7 days after the model production.

4. Statistical Analysis

Evaluation was carried out by a method similar to that of Test Example 3.

5. Test Results

The test compounds exhibited analgesic effect in the formalin-induced prostatitis model.

Test Example 8: Evaluation of PGE2 Production in Prostatic Epithelial Cells Derived from Patient with Benign Prostatic Hyperplasia 1. Cell Culture Prostatic epithelial cells derived from a patient with benign prostatic hyperplasia (BPH-1 cells, Cat. No. ACC143) purchased from DSMZ were subcultured using a growth medium under the conditions of 37° C. and 5% $CO_2$. As the growth medium. RPMI-1640 (Cat. No. 189-02025, manufactured by FUJIFILM Wako Pure Chemical Corporation) containing inactivated fetal bovine serum (Cat. No. SH30910, manufactured by GE Healthcare) at a final concentration of 20%, testosterone (Cat. No. 32811-61, manufactured by NACALAI TESQUE, INC.) at a final concentration of 20 ng/mL, as well as recombinant human insulin at a final concentration of 4.2 μg/mL, human transferrin at a final concentration of 3.8 μg/mL, and sodium selenite at a final concentration of 5 ng/mL (insulin-transferrin-sodium selenite medium supplement, Cat. No. I1884, manufactured by Sigma-Aldrich), was used.

2. Cell Seeding and Drug Treatment

The day before the treatment of each compound to be tested. BPH-1 cells were suspended in the growth medium, and the cells were seeded at 9,600 cells/well on a Falcon (registered trademark) Cell Culture 96-well Multi-well Plate (Cat. No. 353072, manufactured by Corning, Incorporated). In the wells for control, cells were seeded using a control medium. As the control medium, RPMI-1640 (Cat. No. 189-02025, manufactured by FUJIFILM Wako Pure Chemical Corporation) containing inactivated fetal bovine serum (Cat. No. SH30910, manufactured by GE Healthcare) at a final concentration of 2%, testosterone (Cat. No. 32811-61, manufactured by NACALAI TESQUE, INC.) at a final concentration of 20 ng/mL, as well as recombinant human insulin at a final concentration of 4.2 μg/mL, human transferrin at a final concentration of 3.8 μg/mL, and sodium selenite at a final concentration of 5 ng/mL (insulin-transferrin-sodium selenite medium supplement, Cat. No. 11884, manufactured by Sigma-Aldrich), was used. The BPH-1 cells seeded on the 96-well plate were cultured overnight under the conditions of 37° C. and 5% $CO_2$.

The next day after seeding, each substance to be tested was treated. First, a 10 mM DMSO solution was prepared using DMSO (Cat. No. 13445-74, manufactured by NACALAI TESQUE, INC.), and the DMSO solution was diluted to 10, 1, or 0.1 μM using the growth medium. The growth medium or the control medium was removed, the medium in the wells for the growth medium containing each substance to be tested or the wells for control was replaced with the control medium, subsequently the cells were cultured for 48 hours under the conditions of 37° C. and 5% $CO_2$, and the supernatant was collected.

3. Measurement of Amount of PGE2

The amount of PGE2 in the cell culture supernatant was measured according to the manufacturer's protocol by using Prostaglandin E2 kits (Cat. No. 62P2APEG, manufactured by Cisbio) and a microplate reader SpectraMax (registered trademark) M5 (manufactured by Molecular Devices, LLC.).

4. Test Results

The test compounds suppressed PGE2 production in BPH-1 cells.

Preparation Example 1

| Tablet (tablet for internal use) in one 80-mg tablet of formulation, | |
|---|---|
| Test compound | 5.0 mg |
| Corn starch | 46.6 mg |
| Crystalline cellulose | 24.0 mg |
| Methyl cellulose | 4.0 mg |
| Magnesium stearate | 0.4 mg |

A mixed powder of these proportions was tableted by a conventional method to obtain tablets for internal use.

INDUSTRIAL APPLICABILITY

The present invention relates to a prophylactic and/or therapeutic agent for chronic prostatitis/chronic pelvic pain syndrome, the agent containing an mPGES-1 inhibitor as an active ingredient, and the invention has industrial applicability.

The invention claimed is:

1. A method for treating chronic prostatitis/chronic pelvic pain syndrome, the method comprising administering an mPGES-1 inhibitor to a subject in need thereof, wherein the mPGES-1 inhibitor is at least one compound selected from the group consisting of:

N-(3-chloro-2-methylphenyl)-2-(methoxymethyl)-6-({[2-(trifluoromethyl)phenyl]carbonyl}amino)-1H-benzimidazole-4-carboxamide, and N-(3-chloro-2-methylphenyl)-2-[1-(trifluoromethyl)cyclopropyl]-6-({[2-(trifluoromethyl)phenyl]carbonyl}amino)-1H-benzimidazole-4-carboxamide, or a tautomer of the compound, or a pharmaceutically acceptable salt thereof.

2. The method according to claim 1, wherein the mPGES-1 inhibitor is N-(3-chloro-2-methylphenyl)-2-(methoxymethyl)-6-({[2-(trifluoromethyl)phenyl]carbonyl}amino)-1H-benzimidazole-4-carboxamide 4-methylbenzenesulfonate.

3. The method according to claim 1, wherein the mPGES-1 inhibitor is N-(3-chloro-2-methylphenyl)-2-[1-(trifluoromethyl)cyclopropyl]-6-({[2-(trifluoromethyl)phenyl]carbonyl}amino)-1H-benzimidazole-4-carboxamide.

* * * * *